United States Patent
Tsubusaki et al.

(10) Patent No.: US 11,319,408 B2
(45) Date of Patent: May 3, 2022

(54) HYDROPHILIC POLYMER DERIVATIVE HAVING SELF-IMMOLATIVE ACETAL LINKER AND CONJUGATE USING SAME

(71) Applicant: NOF CORPORATION, Tokyo (JP)

(72) Inventors: Takuma Tsubusaki, Kawasaki (JP); Shinya Tamagawa, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 69 days.

(21) Appl. No.: 16/493,033

(22) PCT Filed: Mar. 22, 2018

(86) PCT No.: PCT/JP2018/011485
§ 371 (c)(1),
(2) Date: Sep. 11, 2019

(87) PCT Pub. No.: WO2018/180914
PCT Pub. Date: Oct. 4, 2018

(65) Prior Publication Data
US 2020/0010620 A1     Jan. 9, 2020

(30) Foreign Application Priority Data
Mar. 30, 2017  (JP) .............................. JP2017-067636

(51) Int. Cl.
*C08G 65/331*     (2006.01)
(52) U.S. Cl.
CPC ...... *C08G 65/3311* (2013.01); *C08G 2650/04* (2013.01); *C08G 2650/38* (2013.01); *C08G 2650/64* (2013.01)
(58) Field of Classification Search
CPC ............ C08G 65/3311; C08G 2650/04; C08G 2650/38; C08G 2650/64
See application file for complete search history.

(56) References Cited

U.S. PATENT DOCUMENTS

| | | | |
|---|---|---|---|
| 6,180,095 | B1 | 1/2001 | Greenwald et al. |
| 2001/0031873 | A1 | 10/2001 | Greenwald et al. |
| 2010/0048483 | A1 | 2/2010 | Yang et al. |
| 2012/0142711 | A1 | 6/2012 | Warnecke et al. |
| 2014/0128445 | A1 | 5/2014 | Yang et al. |
| 2016/0046763 | A1 | 2/2016 | Tsubusaki et al. |
| 2018/0078651 | A1 | 3/2018 | Tsubusaki et al. |
| 2018/0298143 | A1 | 10/2018 | Tsubusaki et al. |
| 2020/0289656 | A1 | 9/2020 | Tsubusaki et al. |

FOREIGN PATENT DOCUMENTS

| | | | |
|---|---|---|---|
| CZ | 2007815 | A3 * | 6/2009 |
| JP | 2002-508400 | A | 3/2002 |
| JP | 2012-500804 | A | 1/2012 |
| JP | 2012-530688 | A | 12/2012 |
| JP | 2014-208794 | A | 11/2014 |
| JP | 2016-194057 | A | 11/2016 |
| WO | 99/30727 | A1 | 6/1999 |
| WO | 00/64483 | A2 | 11/2000 |
| WO | 2016/159071 | A1 | 10/2016 |

OTHER PUBLICATIONS

Communication dated Jan. 12, 2021 issued by the European Patent Office in European Application No. 18777041.7.
Lee, S., et al., " Cyclic acetals as cleavable linkers for affinity capture", Organic & Biomolecular Chemistry, vol. 13, No. 31, Jan. 1, 2015, XP055363605, pp. 8445-8452.
Huang, X., et al., "pH-labile sheddable block copolymers by RAFT polymerization: Synthesis and potential use as siRNA conjugates", European Polymer Journal, vol. 49, No. 10, Apr. 16, 2013, XP028711629, pp. 2895-2905.
Richard B. Greenwald et al., Drug Delivery Systems Employing 1,4- or 1,6-Elimination: Poly (ethylene glycol) Prodrugs of Amine-Containing Compounds, Journal of Medical Chemistry, vol. 42, No. 18, 1999, pp. 3657-3667.
International Search Report (PCT/ISA/210) dated May 22, 2018 issued by the International Searching Authority in International Application No. PCT/JP2018/011485.
Written Opinion (PCT/ISA/237) dated May 22, 2018 issued by the International Searching Authority in International Application No. PCT/JP2018/011485.
Communication dated Jul. 26, 2021, from the Japanese Patent Office in Application No. 2018-053824.

* cited by examiner

*Primary Examiner* — Matthew P Coughlin
(74) *Attorney, Agent, or Firm* — Sughrue Mion, PLLC

(57) ABSTRACT

To provide a hydrophilic polymer derivative having a novel linker technique which is able to from a hydrophilic polymer pro-drug of a drug containing an amino group or the like in order to overcome the restrictions of conventional hydrophilic polymer pro-drugs. A hydrophilic polymer derivative containing a hydrophilic polymer moiety and an acetal moiety, wherein the hydrophilic polymer derivative contains a structure represented by formula (1) or formula (2):

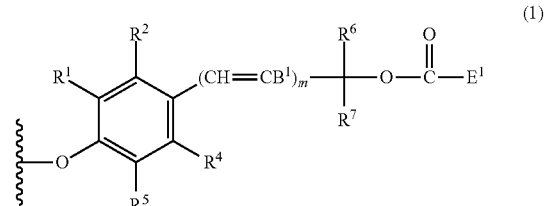

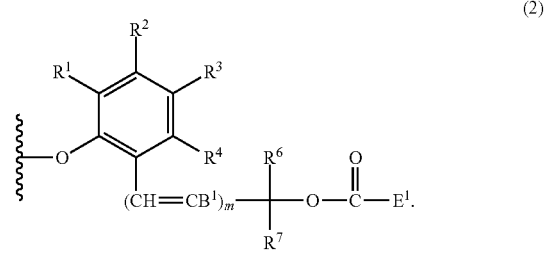

14 Claims, 6 Drawing Sheets

HYDROPHILIC POLYMER DERIVATIVE HAVING SELF-IMMOLATIVE ACETAL LINKER AND CONJUGATE USING SAME

CROSS REFERENCE TO RELATED APPLICATIONS

This application is a National Stage of International Application No. PCT/JP2018/011485 filed Mar. 22, 2018, claiming priority based on Japanese Patent Application No. 2017-067636 filed Mar. 30, 2017.

TECHNICAL FIELD

The present invention relates to a hydrophilic polymer derivative, which is used for pro-drug modification of a biofunctional molecule, for example, a physiologically active protein, a peptide, an antibody, a nucleic acid or a low molecular weight drug, or a drug carrier, for example, a liposome or a polymeric micelle, and a conjugate using the same.

BACKGROUND ART

In drug delivery system, the chemical modification of biofunctional molecule or drug carrier with a hydrophilic polymer having low antigenicity has an advantage, for example, improvement in water solubility of these drugs and the like, avoidance of kidney clearance or suppression of degradation by a metabolic enzyme, and is an effective technique for prolonging circulation time of the drug or the like in blood and for increasing bioavailability. On the other hand, it is known that in the drug or the like to which a hydrophilic polymer is permanently bonded by a covalent bond, because of the formation of a hydration layer or the steric shielding effect on the active site by the hydrophilic polymer, the interaction with a living body endogenous molecule, a receptor or a cell membrane as a target is decreased and the undesirable effect, for example, the decrease in the intrinsic pharmacological action of the drug or the change in pharmacokinetics or intracellular kinetics may occur on the drug or the like.

As an approach to the problems as described above, a method in which the drug or the like is chemically modified with a hydrophilic polymer through a temporary linkage and the temporary linkage is cleaved in the living body to release the non-chemically modified active drug or the like, that is, a pro-drug modification method is used "Bioconjugate Chemistry 2015, 26 (7), 1172-1181". One of the most promising methods is a pro-drug modification method in which the cleavage occurs by a cascade mechanism.

The cleavage by a cascade mechanism becomes possible by a linker structure composed of a combination of a masking group and an activating group (FIG. 1). The masking group is bonded to the activating group by a first temporary linkage. The activating group is bonded to an amino group present in the drug or the like through a second temporary linkage. The stability of the second temporary linkage largely depends on whether the masking group is present or not. In the presence of the masking group, the second temporary linkage is very stable and the release of the drug bonded usually cannot occur. On the other hand, in the case where the masking group is not present, the second temporary linkage becomes very unstable and is rapidly cleaved to release the drug. Accordingly, the activating group is also referred to as a self-immolative spacer. As described above, in the cleavage by a cascade mechanism the cleavage of the first temporary linkage between the masking group and the activating group is a rate-determining step.

As the masking group, an atomic group in which the first temporary linkage is cleaved by using as a trigger, the environmental characteristics in each portion of the living body, that is, the environmental stimulation, for example, the presence or absence of a specific enzyme or the reductive environment is frequently used. Further, one of the most frequently used activating groups is an atomic group based on 1,4- or 1,6-benzyl elimination.

In Patent Literature 1, examples of a hydrophilic polymer pro-drug in which a carbamate group, an amide group or an oligopeptide group is introduced as the masking group and 2-aminobenzyl alcohol or 4-aminobenzyl alcohol is used as the activating group are disclosed (FIG. 2 and FIG. 3). Here, the enzymatic or non-enzymatic hydrolysis of the carbamate bond or amide bond (peptide bond) which is the first temporary linkage between the masking group and the activating group triggers the cleavage of the carbamate bond which is the second temporary linkage between 2-aminobenzyl alcohol or 4-aminobenzyl alcohol and the drug based on the 1,4- or 1,6-benzyl elimination to release the drug. In the process of releasing the drug, 2-aminobenzyl alcohol or 4-aminobenzyl alcohol and carbon dioxide are liberated.

Further, in Patent Literature 2, examples of a hydrophilic polymer pro-drug in which a disulfide group is introduced as the masking group and 2-mercaptobenzyl alcohol or 4-mercaptobenzyl alcohol is used as the activating group are disclosed. Here, the reductive cleavage of the disulfide bond which is the first temporary linkage between the masking group and the activating group triggers the cleavage of the carbamate bond which is the second temporary linkage between 2-mercaptobenzyl alcohol or 4-mercaptobenzyl alcohol and the drug based on the 1,4- or 1,6-benzyl elimination to release the drug. In the process of releasing the drug, 2-mercaptobenzyl alcohol or 4-mercaptobenzyl alcohol and carbon dioxide are liberated. An example thereof is shown in FIG. 4.

The hydrophilic polymer pro-drugs disclosed in Patent Literature 1 and Patent Literature 2 liberate aminobenzyl alcohol and mercaptobenzyl alcohol, respectively, in the process of releasing the drug. The amino group of the aminobenzyl alcohol is protonated at pH in the living body to be positively charged so that it has a possibility to interact with a cell membrane which is ordinarily negatively charged. Further, the mercapto group of the mercaptobenzyl alcohol has a possibility to cause an exchange reaction with a disulfide bond present in a protein. Therefore, the drug or the like in which the hydrophilic polymer is modified through these linker structures has an undesirable aspect, in that the necessity of evaluation of secondary interaction after the aminobenzyl alcohol or mercaptobenzyl alcohol is liberated arises, in that analysis of the pharmacological activity of the drug or the like is complicated, or the like.

On the other hand, in Non Patent Literature 1, examples of a hydrophilic polymer pro-drug in which an ester group or a carbonate group is introduced as the masking group and 2-hydroxybenzyl alcohol or 4-hydroxybenzyl alcohol is used as the activating group are disclosed. Here, the enzymatic or non-enzymatic hydrolysis of the ester bond or carbonate bond which is the first temporary linkage between the masking group and the activating group triggers the cleavage of the carbamate bond which is the second temporary linkage between 2-hydroxybenzyl alcohol or 4-hydroxybenzyl alcohol and the drug based on the 1,4- or 1,6-benzyl elimination to release the drug. In the process of releasing the drug, 2-hydroxybenzyl alcohol or 4-hydroxybenzyl alcohol and carbon dioxide are liberated. An example thereof is shown in FIG. 5.

The functional group contained in the hydroxybenzyl alcohol liberated is only the hydroxy group and unlike the aminobenzyl alcohol and mercaptobenzyl alcohol of Patent Literature 1 and Patent Literature 2, the interaction with a cell membrane or a protein is very small.

However, since the linker structure disclosed in Non Patent Literature 1 uses an ester group or a carbonate group as the masking group, the enzyme-dependent cleavage (hydrolysis) in blood rapidly occurs and a conflict between the original purpose of the chemical modification with a hydrophilic polymer to prolong the blood circulation time of the drug or the like causes. A further disadvantage of the enzyme-dependent cleavage is variability between patients. Since the enzyme level can be significantly different between individuals, biological variation arises in the release of the drug or the like from the pro-drug by the enzyme-dependent cleavage. Further, since the enzyme level can vary depending on the site of administration, the drug design is very difficult.

Moreover, in Non Patent Literature 1, it is described that a problem potentially exists in that during the binding reaction between the activating group and an amino group of the drug or the like, the eater group or carbonate group causes a side reaction with the amino group to generate undesirable by-products. Since such by-products have a large influence on the pharmacokinetics or physical properties of the drug or the like, the by-products are required to be removed prior to formulation, but the separation removal thereof is a major hurdle from a technical standpoint and a cost standpoint in the case of production on an industrial scale.

PRIOR ART LITERATURES

Patent Literatures

Patent Literature 1: International Publication No. 1999/030727
Patent Literature 2: International Publication No. 2000/064483

Non Patent Literature

Non-Patent Literature 1: Journal of Medical Chemistry 1999, 42(18), 3657-3667

SUMMARY OF INVENTION

Problem to be Solved by the Invention

An object of the invention is to provide a hydrophilic polymer derivative having a novel linker technique which is able to from a hydrophilic polymer pro-drug of a drug containing an amino group or the like in order to overcome the restrictions of conventional hydrophilic polymer pro-drugs as described above, and a conjugate using the same.

Means for Solving the Problem

As a result of the intensive investigations to solve the problem described above, the inventors have developed a hydrophilic polymer derivative which has an acetal structure capable of being cleaved depending on only pH and is capable of releasing a drug or the like, which has not been chemically modified, caused by the cleavage of the acetal.

Further, the invention has a feature in that since a low-molecular compound liberated in the process of releasing the drug or the like is a benzyl alcohol derivative having only a hydroxy group as the functional group, the secondary interaction in the living body is hard to occur. Further, since the acetal structure is basically inert to the amino group, there is also an advantage in that a by-product does not generate in the binding reaction with the drug or the like having an amino group.

Thus, the present invention is as follows.

[1] A hydrophilic polymer derivative containing a hydrophilic polymer moiety and an acetal moiety, wherein the hydrophilic polymer derivative contains a structure represented by formula (1) or formula (2):

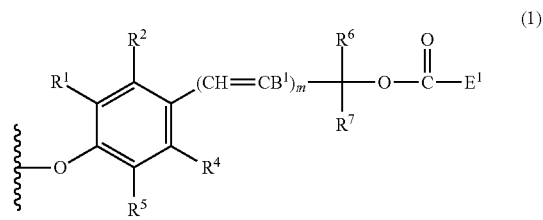

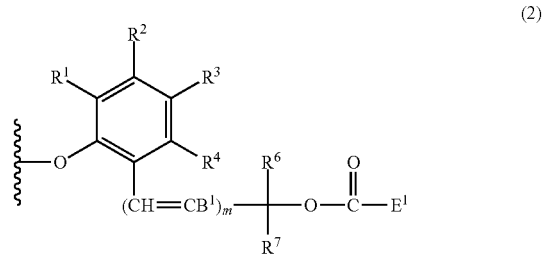

(in formula (1) and formula (2), $B^1$ is a hydrogen atom or $-C(R^6)(R^7)OC(O)E^1$; $E^1$ is a leaving group; $R^1$ is a hydrocarbon group having from 1 to 10 carbon atoms or a hydrogen atom, or $R^1$ may be bonded to an oxygen atom of the acetal moiety; $R^2$, $R^3$, $R^4$, $R^5$, $R^6$ and $R^7$ are each independently a hydrocarbon group having from 1 to 10 carbon atoms or a hydrogen atom; m is 0 or 1; one of two oxygen atoms contained in the acetal moiety is bonded to the phenyl group; and a wavy line represents a covalent bond to a carbon atom bonded to both of the oxygen atoms contained in the acetal moiety.)

[2] The hydrophilic polymer derivative of [1], which is represented by formula (3) or formula (4):

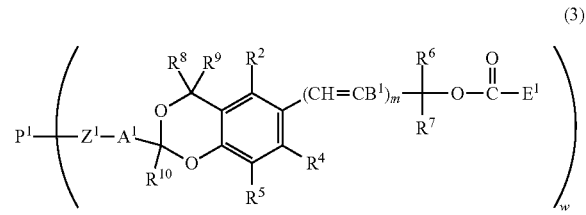

-continued

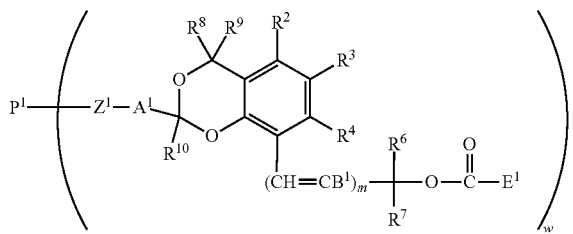

(4)

(in formula (3) and formula (4), $P^1$ is the hydrophilic polymer moiety; w is an integer of 1 to 20; $Z^1$ is an ether bond, an ester bond, a carbonate bond, a urethane bond, an amide bond, a secondary amino group, an alkylene group containing any of these bonds and group, a single bond or an alkylene group, and in the case where $Z^1$ is an ether bond, an ester bond, a carbonate bond, a urethane bond, an amide bond, a secondary amino group or an alkylene group containing any of these bonds and group and a plurality of identical structural units are connected, a number of the structural units described above is 2 or less; $A^1$ is a divalent hydrocarbon group having from 1 to 10 carbon atoms or a phenylene group which may have a substituent; $R^8$ and $R^9$ are each independently a hydrocarbon group having from 1 to 9 carbon atoms or a hydrogen atom; and $R^{10}$ is a hydrocarbon group having from 1 to 10 carbon atoms or a hydrogen atom.)

[3] The hydrophilic polymer derivative of [1], which is represented by formula (5) or formula (6):

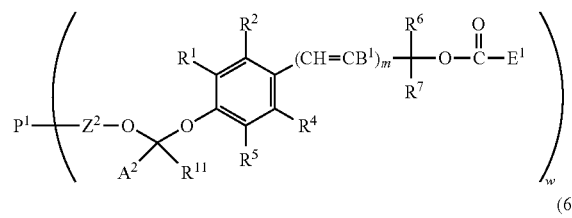

(5)

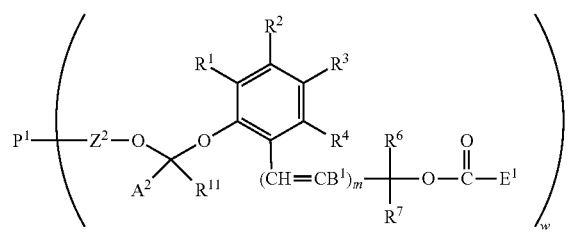

(6)

(in formula (5) and formula (6), $P^1$ is the hydrophilic polymer moiety; w is an integer of 1 to 20; $Z^2$ is an ether bond, an ester bond, a carbonate bond, a urethane bond, an amide bond, a secondary amino group, an alkylene group containing any of these bonds and group, a single bond or an alkylene group, and in the case where $Z^2$ is an ether bond, an ester bond, a carbonate bond, a urethane bond, an amide bond, a secondary amino group or an alkylene group containing any of these bonds and group and a plurality of identical structural units are connected, a number of the structural units is 2 or less; $A^2$ is a hydrocarbon group having from 1 to 10 carbon atoms or a phenylene group which may have a substituent; and $R^{11}$ is a hydrocarbon group having from 1 to 10 carbon atoms or a hydrogen atom.)

[4] The hydrophilic polymer derivative of [2] or [3], wherein $P^1$ is a straight-chain polyethylene glycol having a hydrocarbon group or a chemically reactive functional group at a terminal.

[5] The hydrophilic polymer derivative of [4], wherein w is 1 and $P^1$ is represented by formula (7) or formula (8):

(7)

(in formula (7), $Y^1$ is a hydrocarbon group having from 1 to 24 carbon atoms, and n is an integer of 3 to 2,000);

(8)

(in formula (8), $X^1$ is a chemically reactive functional group, $Z^3$ is a divalent spacer, and n is an integer of 3 to 2,000.)

[6] The hydrophilic polymer derivative of [2] or [3], wherein $P^1$ is a branched polyethylene glycol having a hydrocarbon group or a chemically reactive functional group at a terminal.

[7] The hydrophilic polymer derivative of [6], wherein w is 1 and $P^1$ is represented by formula (9) or formula (10):

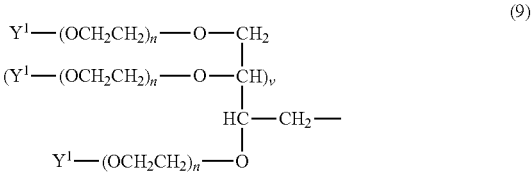

(9)

(in formula (9), $Y^1$ is a hydrocarbon group having from 1 to 24 carbon atoms, n is an integer of 3 to 1,000, and v is 0 or 2);

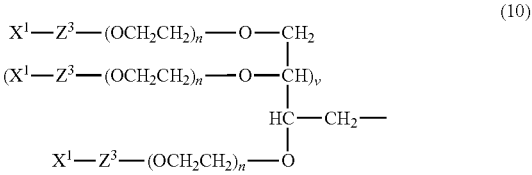

(10)

(in formula (10), $X^1$ is a chemically reactive functional group, $Z^3$ is a divalent spacer, n is an integer of 3 to 1,000, and v is 0 or 2.)

[8] The hydrophilic polymer derivative of [6], wherein w is v+2 and $P^1$ is represented by formula (11):

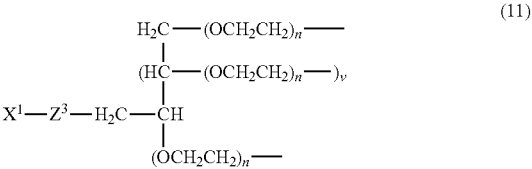

(11)

(in formula (11), $X^1$ is a chemically reactive functional group, $Z^3$ is a divalent spacer, n is an integer of 3 to 1,000, and v is 0 or 2.)

[9] The hydrophilic polymer derivative of [5], [7] or [8], wherein $X^1$ is selected from the group consisting of a maleimide group, an α-haloacetyl group, an acryl group, a vinyl sulfone group, a protected thiol group, a pyridyldithio group, an aldehyde group, a carboxy group, a protected carboxy group, a protected amino group, a protected oxyamino group, a protected hydrazide group, an azide group, an allyl group, a vinyl group, an alkynyl group and a hydroxy group.

[10] The hydrophilic polymer derivative of [5], [7] or [8], wherein $X^1$ is selected from the group consisting of formula (a), formula (b), formula (c), formula (d), formula (e), formula (f), formula (g), formula (h), formula (i), formula (j), formula (k), formula (l), formula (m), formula (n) and formula (o):

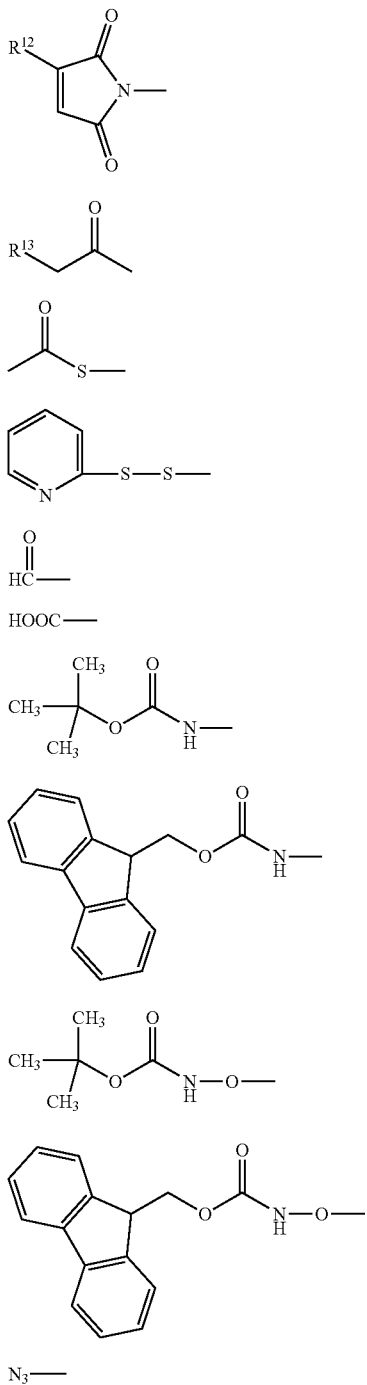

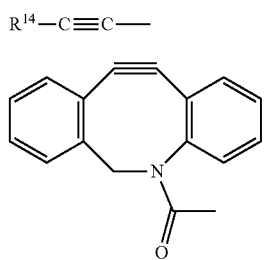

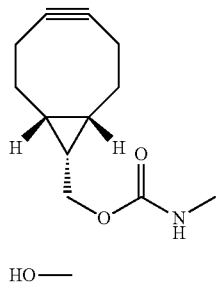

(in formula (a), $R^{12}$ is a hydrogen atom or a hydrocarbon group having from 1 to 5 carbon atoms; in formula (b), $R^{13}$ is a halogen atom selected from a chlorine atom, a bromine atom and an iodine atom; and in formula (l), $R^{14}$ is a hydrogen atom or a hydrocarbon group having from 1 to 5 carbon atoms.)

[11] The hydrophilic polymer derivative of [5], [7] or [8], wherein $Z^3$ is an ether bond, an ester bond, a carbonate bond, a urethane bond, an amide bond, a secondary amino group, an alkylene group containing any of these bonds and group, a single bond or an alkylene group, and in the case where $Z^3$ is an ether bond, an ester bond, a carbonate bond, a urethane bond, an amide bond, a secondary amino group or an alkylene group containing any of these bonds and group and a plurality of identical structural units are connected, a number of the structural units is 2 or less.

[12] The hydrophilic polymer derivative of [2] or [3], wherein $P^1$ is a polyethylene glycol having a number of terminals of 2 to 8, all the terminals of the polyethylene glycol constituting $P^1$ are each connected to $Z^1$, and w is equal to the number of terminals of the polyethylene glycol.

[13] The hydrophilic polymer derivative of [12], wherein $P^1$ is selected from the group consisting of formula (r), formula (s), formula (t), formula (u) and formula (v):

-continued

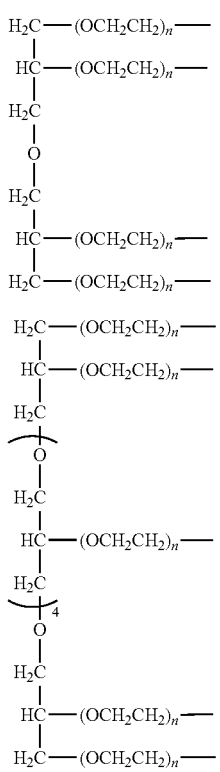

(in the formulae, n is an integer of 3 to 2,000, w is 2 in the case where $P^1$ is represented by formula (r), w is 3 in the case where $P^1$ is represented by formula (s), w is 4 in the case where $P^1$ is represented by formula (t), w is 4 in the case where $P^1$ is represented by formula (u), and w is 8 in the case where $P^1$ is represented by formula (v).)

[14] A conjugate having a structure represented by formula (12) or formula (13) which is obtained by reacting the —OC(O)$E^1$ group of the hydrophilic polymer derivative of any one of [1] to [13] with an amino group contained in a biofunctional molecule:

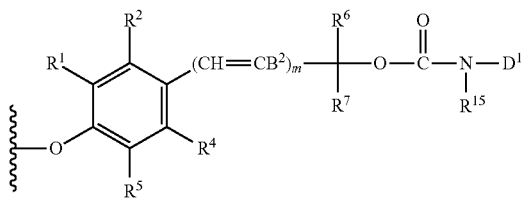

(12)

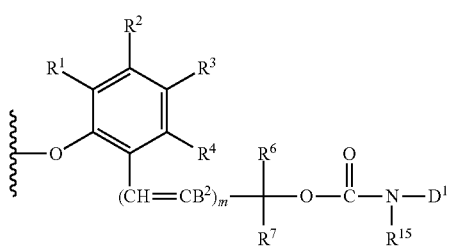

(13)

(in formula (12) and formula (13), $B^2$ is a hydrogen atom or —C($R^6$)($R^7$)OC(O)$D^1$; $R^1$ is a hydrocarbon group having from 1 to 10 carbon atoms or a hydrogen atom, or $R^1$ may be bonded to an oxygen atom of the acetal moiety; $R^2$, $R^3$, $R^4$, $R^5$, $R^6$, $R^7$ and $R^5$ are each independently a hydrocarbon group having from 1 to 10 carbon atoms or a hydrogen atom; m is 0 or 1; a wavy line represents a covalent bond to a carbon atom bonded to both of the oxygen atoms contained in the acetal moiety; and $D^1$ is a residue obtained by eliminating an amino group constituting a carbamate bond among amino groups contained in the biofunctional molecule.)

Effect of the Invention

The hydrophilic polymer derivative having a self-immolative acetal linker according to the invention has an acetal structure capable of being cleaved depending on only pH and is capable of releasing a drug or the like, which has not been chemically modified, caused by the cleavage of the acetal. Therefore, control of the release behavior of the dug or the like from a pro-drug modified with the hydrophilic polymer derivative is easy and further, since the drug or the like released is not chemically modified, the pharmacological action thereof is exhibited without imparting the pharmacological action thereof.

Further, as to the pre-drug using the hydrophilic polymer derivative, the secondary interaction of a benzyl alcohol derivative liberated in the process of releasing the drug or the like in the living body is hard to occur, so that the drug design is simple and in addition, since the acetal structure is basically inert to the amino group, a by-product does not generate in the binding reaction with the drug or the like having an amino group, so that the production on an industrial scale is easy.

EMBODIMENTS FOR CARRYING OUT THE INVENTION

Figure 1:
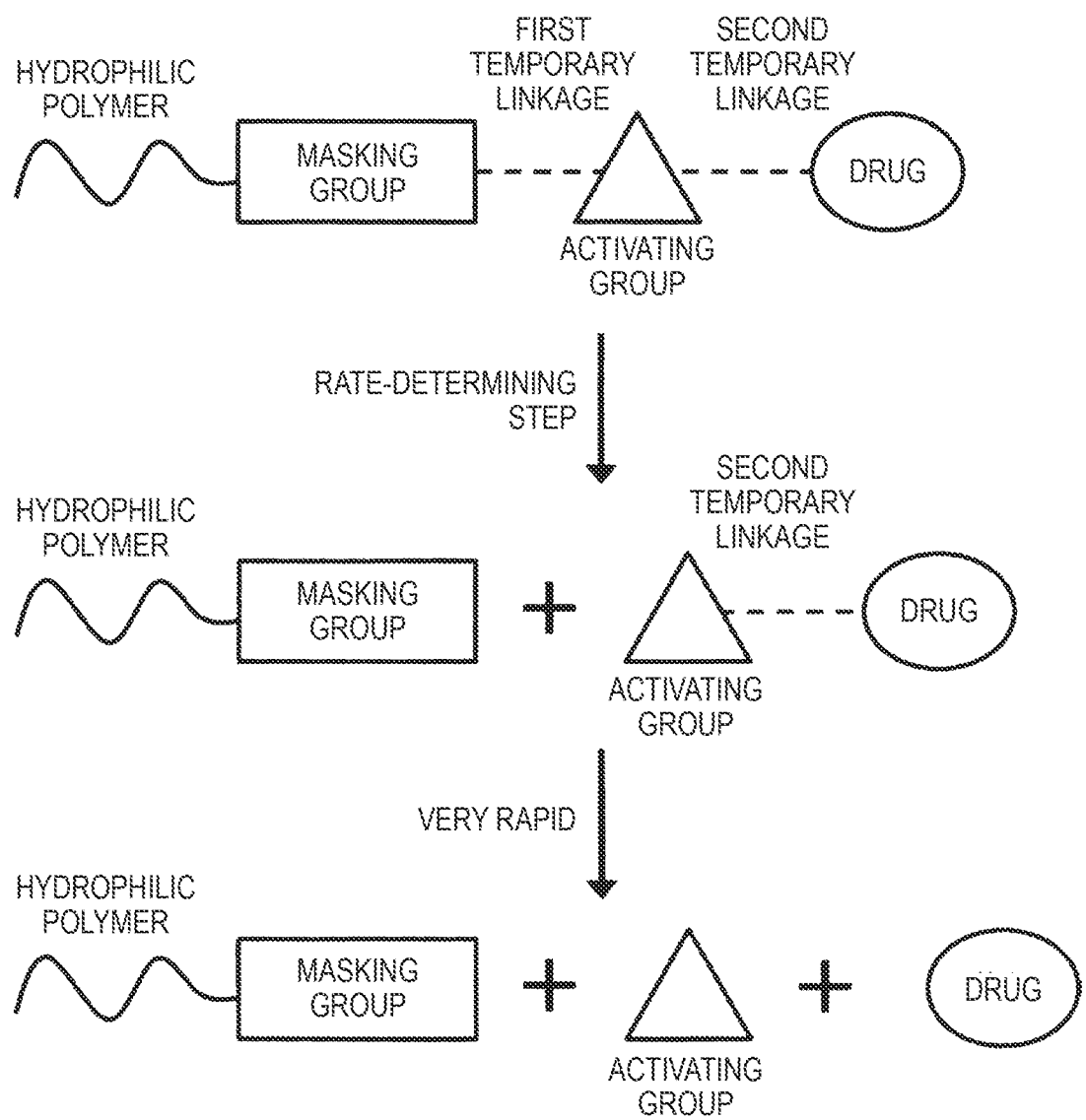
FIG. 1 is a diagram showing drug release of a hydrophilic polymer pro-drug by a cascade mechanism.
Figure 2:
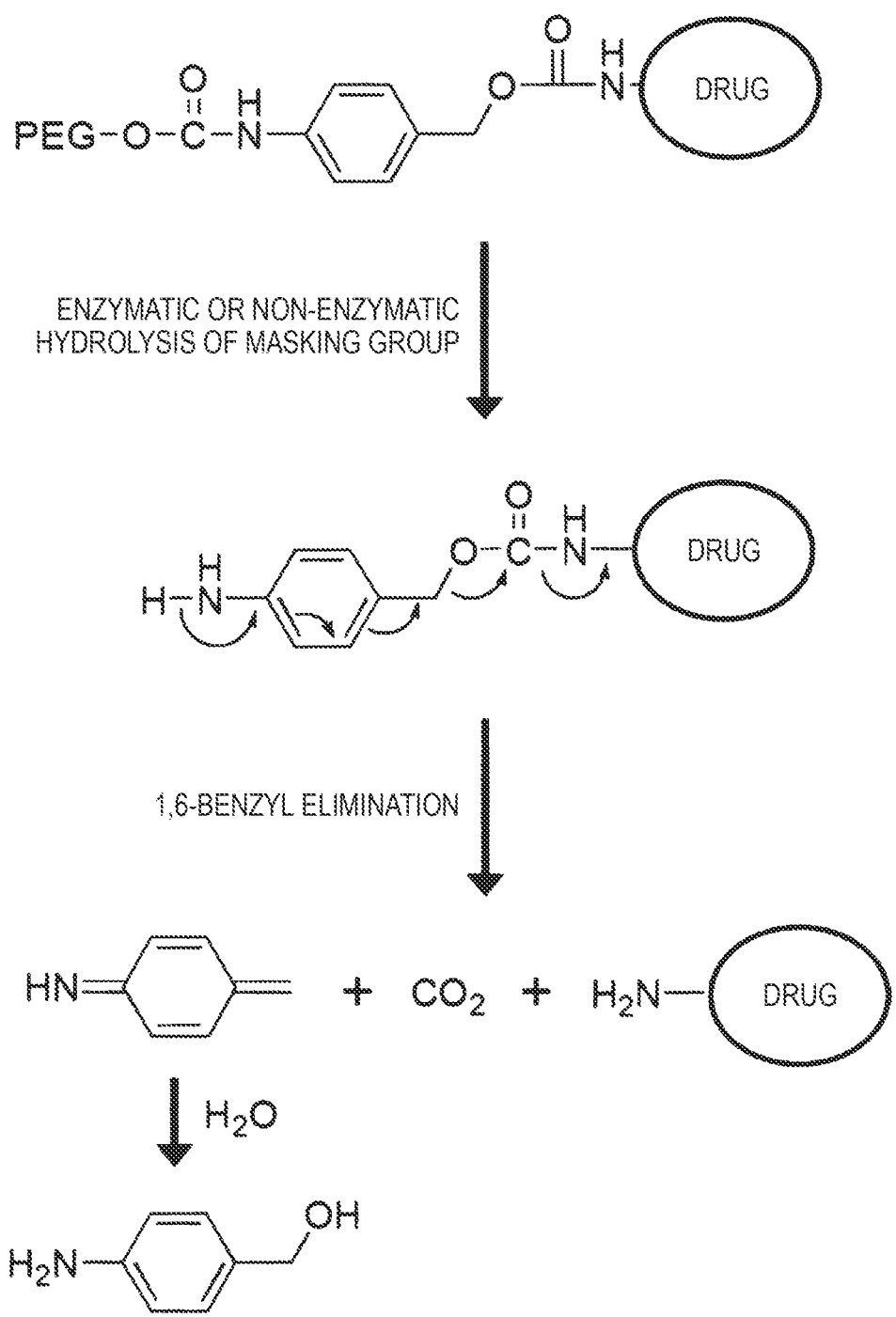
FIG. 2 is a diagram showing cleavage of a pro-drug using 4-aminobenzyl alcohol based on 1,6-benzyl elimination.
Figure 3:
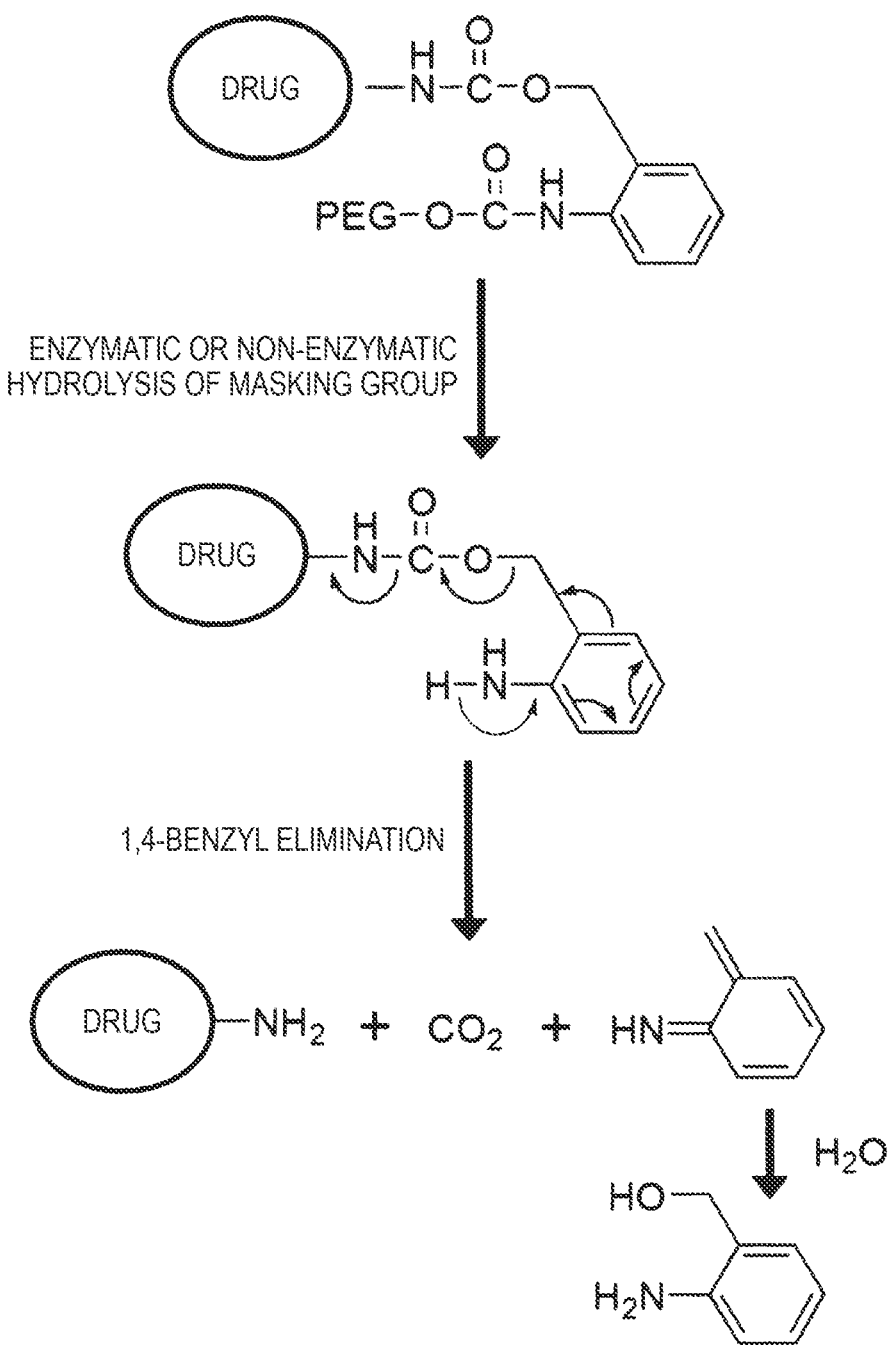
FIG. 3 is a diagram showing cleavage of a pro-drug using 2-aminobenzyl alcohol based on 1,4-benzyl elimination.
Figure 4:
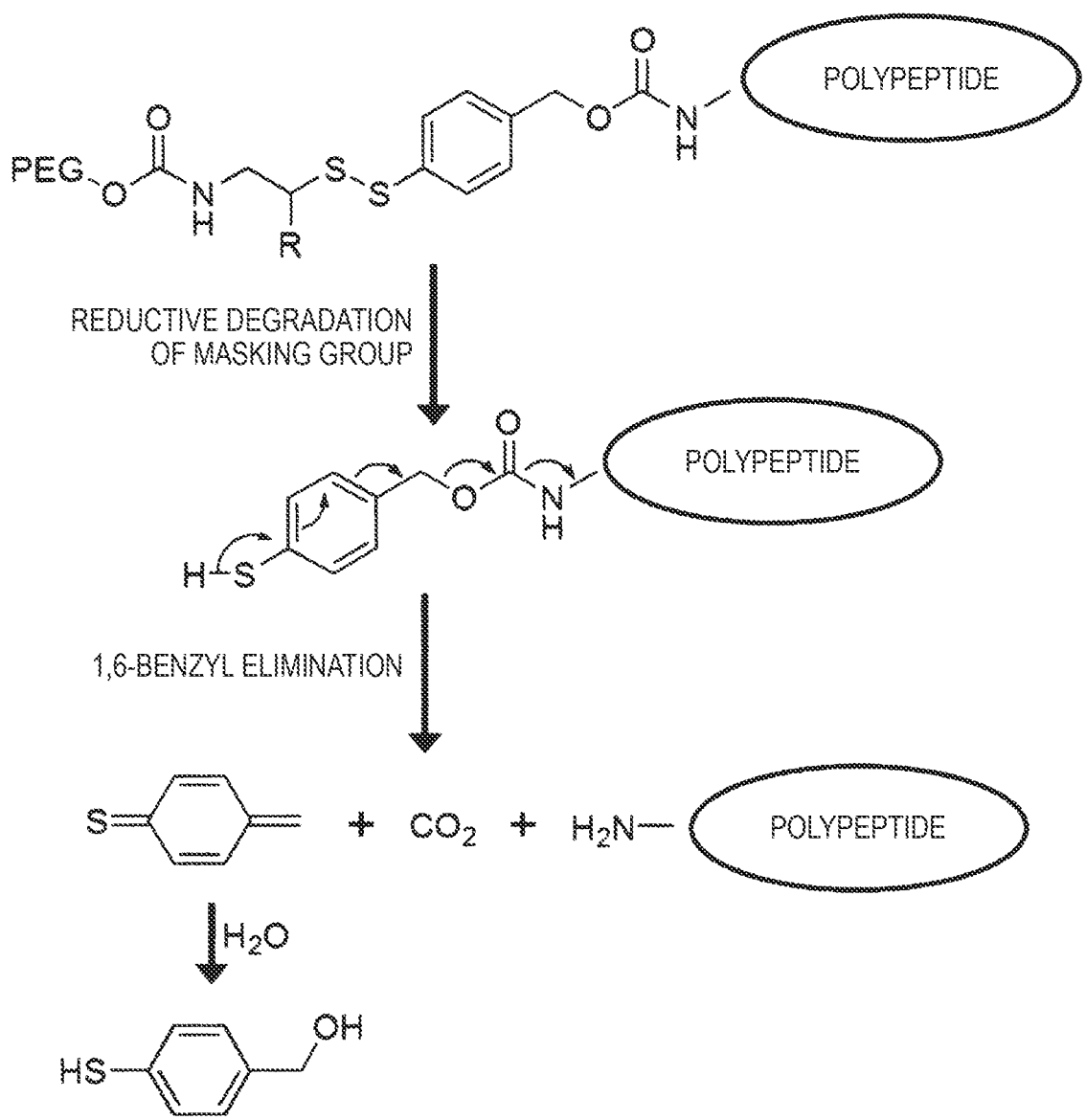
FIG. 4 is a diagram showing cleavage of a pro-drug using 6-mercaptobenzyl alcohol based on 1,6-benzyl elimination.
Figure 5:
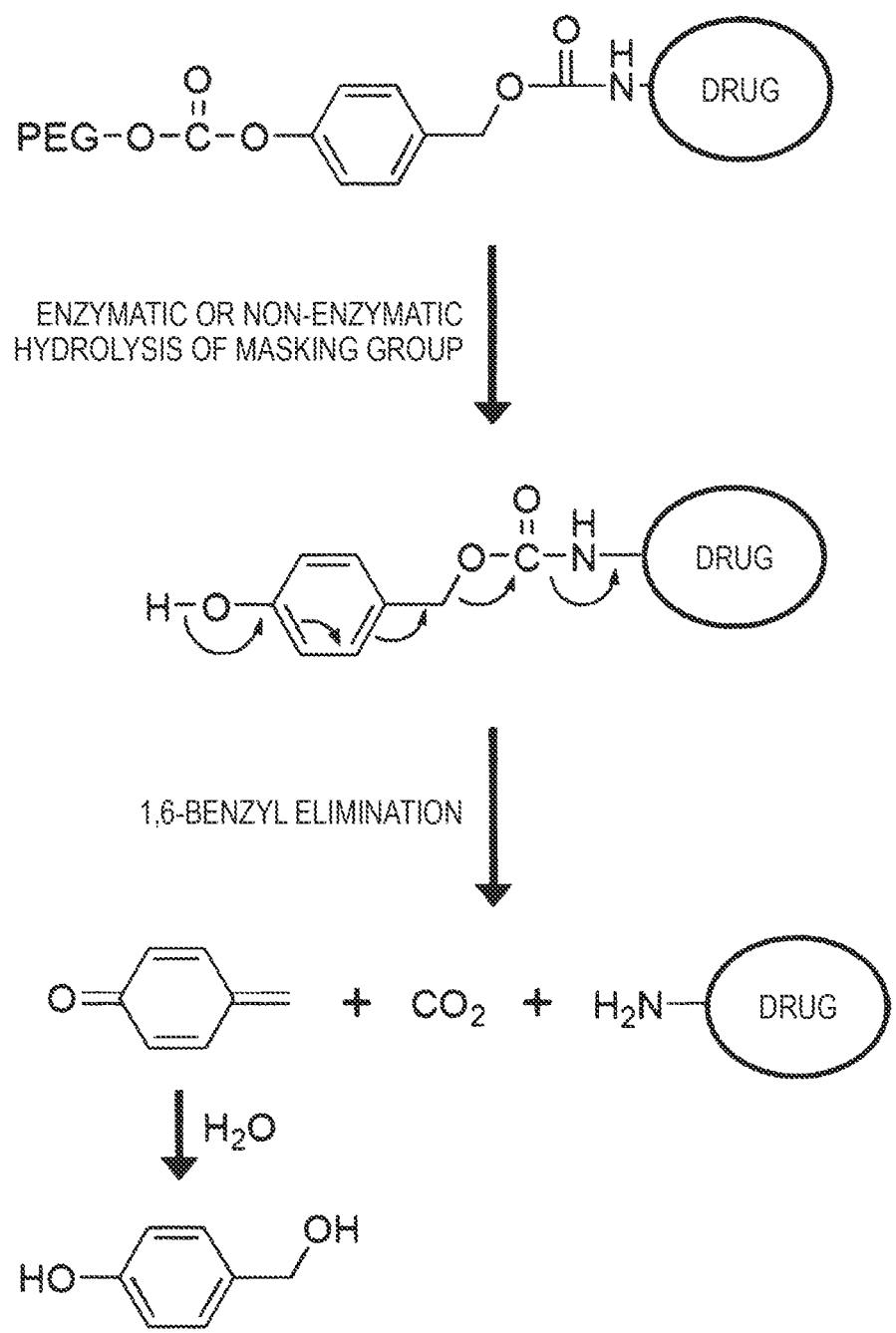
FIG. 5 is a diagram showing cleavage of a pro-drug using 6-hydroxybenzyl alcohol based on 1,6-benzyl elimination.

The invention will be described in detail hereinafter.

The term "acetal moiety" as used in the specification means both of an acetal structure derived from an aldehyde and an acetal structure derived from a ketone, that is, a ketal structure.

The term "pro-drug" as used in the specification is an optional compound which exhibits its pharmacological effect after being subjected to biotransformation. Therefore, the pro-drug is a drug including a specialized protective group which is used in a temporary manner to modify or eliminate undesirable properties in the parent molecule.

The term "cascade mechanism" as used in the specification means a cleavage mechanism of pro-drug in which the activating group is subjected to unmasking to cause release of the drug for the first time.

The hydrophilic polymer derivative having a self-immolative acetal linker of the invention has an active carbonate group at the terminal through an acetal moiety, and of two ether parts constituting the acetal moiety, the ether part having the active carbonate group at the terminal contains a structure represented by formula (1) or formula (2).

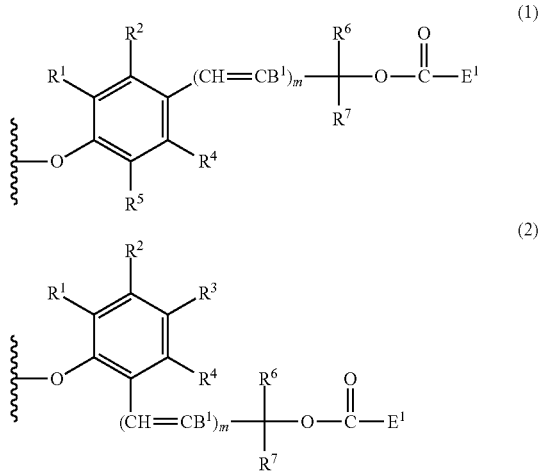

(1)

(2)

The active carbonate group in the invention is a functional group represented by "—O—C(=O)-E¹" in formula (1) or formula (2) and indicates an activated carbonate group. $E^1$ represents a leaving group.

The active carbonate group preferably reacts with an amino group contained in a biofunctional molecule or a drug carrier to from a carbamate bond. Preferred examples of $E^1$ include a succinimidyloxy group, a phthalimidyloxy group, a 4-nitrophenoxy group, a 1-imidazolyl group, a pentafluorophenoxy group, a benzotriazol-1-yloxy group and a 7-azabenzotriazol-1-yloxy group. $E^1$ is more preferably a succinimidyl group, a 4-nitrophenoxy group, a 1-imidazolyl group or a pentafluorophenoxy group, and still more preferably a succinimidyl group or a 4-nitrophenoxy group.

Specific examples of the hydrophilic polymer constituting the hydrophilic polymer moiety $P^1$ in the invention include polyalkylene glycol, polyoxazoline, polycarbonate, polyurethane, polyvinyl alcohol, polyacrylate, polymethacrylate, polyacrylamide, polyvinyl pyrrolidone, polylactic acid, polyglycolic acid, polyamino acid and copolymers derived from the polymers described above. The hydrophilic polymer is preferably a polyalkylene glycol, and more preferably polyethylene glycol.

The polyethylene glycol constituting $P^1$ includes both of polyethylene glycol having a molecular weight distribution obtained by polymerization of ethylene oxide and a monodispersed polyethylene glycol obtained by connecting of an oligoethylene glycol having a single molecular weight by a coupling reaction.

$R^2$, $R^3$, $R^4$, $R^5$, $R^6$ and $R^7$ in formula (1) or formula (2) of the invention are each independently a hydrocarbon group having from 1 to 10 carbon atoms or a hydrogen atom. Specific examples of the hydrocarbon group include a methyl group, an ethyl group, a propyl group, an isopropyl group, a tert-butyl group, a phenyl group and a benzyl group. A preferred embodiment of $R^2$, $R^3$, $R^4$, $R^5$, $R^6$ or $R^7$ is a hydrogen atom or a methyl group, and more preferably a hydrogen atom.

$R^1$ in formula (1) or formula (2) of the invention is a hydrocarbon group having from 1 to 10 carbon atoms or a hydrogen atom. $R^1$ may be bonded to an oxygen atom of the acetal moiety. In a preferred aspect of the invention, $R^1$ is a divalent hydrocarbon group having from 1 to 10 carbon atoms and specifically includes a methylene group, a monoalkylmethylene group, a dialkylmethylene group, an ethylene group, a monoalkylethylene group, a dialkylethylene group, a propylene group, a monoalkylpropylene group and a dialkylpropylene group. $R^1$ is preferably a methylene group, an ethylene group or a propylene group, more preferably a methylene group or an ethylene group, and still more preferably a methylene group.

m in formula (1) or formula (2) of the invention is 0 or 1. In a preferred embodiment, m is 0, and a hydrophilic polymer derivative represented by formula (14) or formula (15) is provided.

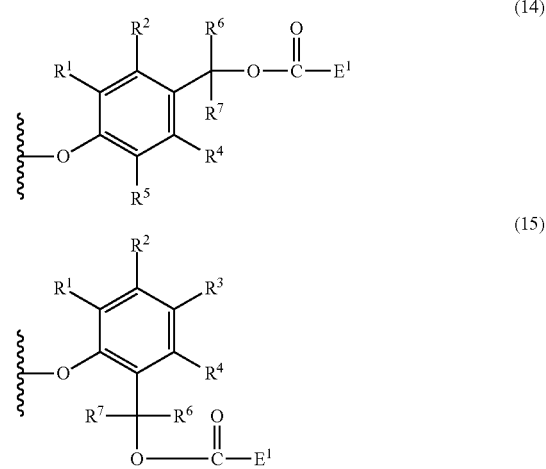

(14)

(15)

In another preferred embodiment of the aspect, m is 1 and $B^1$ is a hydrogen atom, and a hydrophilic polymer derivative represented by formula (16) or formula (17) is provided.

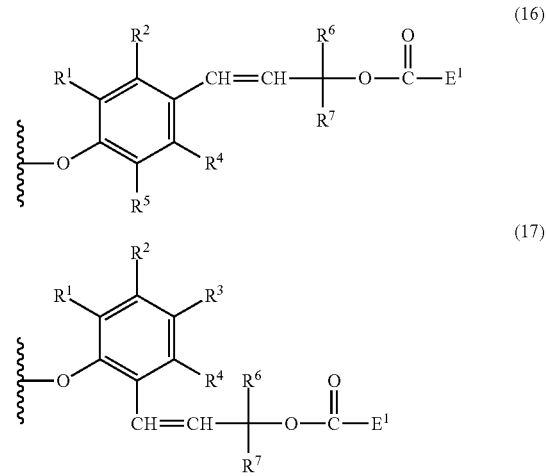

(16)

(17)

In still another preferred embodiment of the aspect, m is 1 and $B^1$ is —$C(R^6)(R^7)OC(O)E^1$, and a hydrophilic polymer derivative represented by formula (18) or formula (19) is provided. In the embodiment, a derivative having two $E^1$ with respect to one acetal is provided.

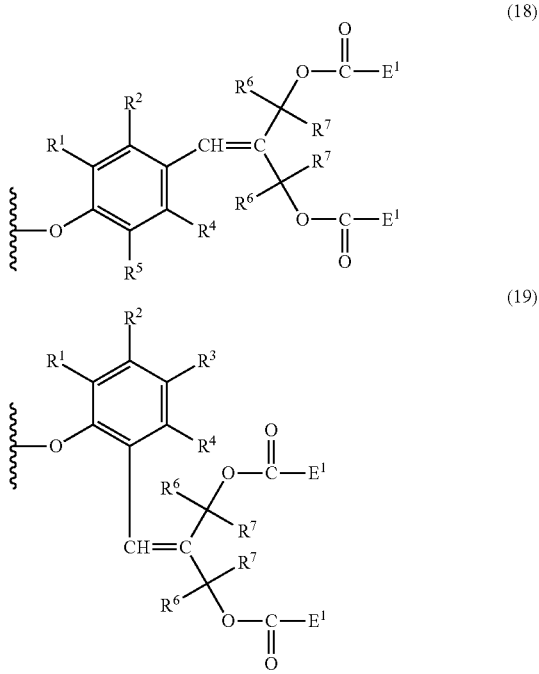

(18)

(19)

In one aspect of the invention, a hydrophilic polymer derivative represented by formula (3) or formula (4) is provided.

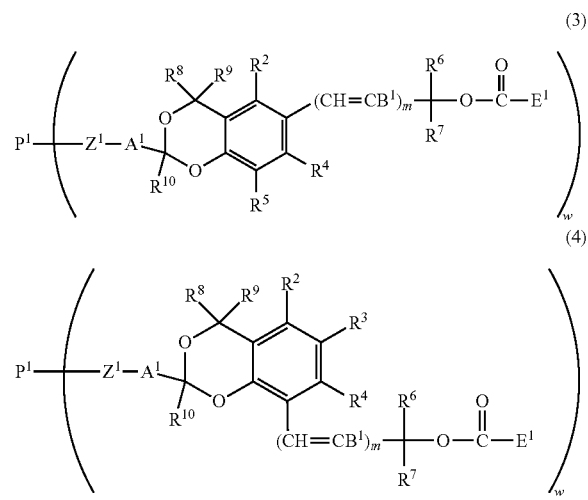

(3)

(4)

$R^2$, $R^3$, $R^4$, $R^5$, $R^6$, $R^7$ and $R^{10}$ in formula (3) or formula (4) of the aspect are each independently a hydrocarbon group having from 1 to 10 carbon atoms or a hydrogen atom. Specific examples of the hydrocarbon group of $R^2$, $R^3$, $R^4$, $R^5$, $R^6$, $R^7$ or $R^{10}$ include a methyl group, an ethyl group, a propyl group, an isopropyl group, a tert-butyl group, a phenyl group and a benzyl group. A preferred embodiment of $R^2$, $R^3$, $R^4$, $R^5$, $R^6$, $R^7$ or $R^{10}$ is a hydrogen atom or a methyl group, and more preferably a hydrogen atom.

$R^8$ and $R^9$ in formula (3) or formula (4) of the aspect are each independently a hydrocarbon group having from 1 to 9 carbon atoms or a hydrogen atom. Specific examples of the hydrocarbon group of $R^8$ or $R^9$ include a methyl group, an ethyl group, a propyl group, an isopropyl group, a tert-butyl group, a phenyl group and a benzyl group. A preferred embodiment of $R^8$ or $R^9$ is a hydrogen atom or a methyl group, and more preferably a hydrogen atom.

$A^1$ in formula (3) or formula (4) of the aspect is a divalent hydrocarbon group having from 1 to 10 carbon atoms or a phenylene group which may have a substituent. Specific examples of the hydrocarbon group include a methylene group, an ethylene group, a propylene group and a butylene group. The phenylene group may be a 1,2-phenylene group, a 1,3-phenylene group or a 1,4-phenylene group. The substituent for the phenylene group may be any of an electron-withdrawing substituent and an electron-donating substituent and may be used individually or in combination as long as the substituent does not cause a side reaction in the synthesis process of the hydrophilic polymer derivative.

The electron-withdrawing substituent includes an acyl group having from 2 to 5 carbon atoms, an alkoxycarbonyl group having from 2 to 5 carbon atoms, a carbamoyl group having from 2 to 5 carbon atoms, an acyloxy group having from 2 to 5 carbon atoms, an acylamino group having from 2 to 5 carbon atoms, an alkoxycarbonylamino group having from 2 to 5 carbon atoms, a fluorine atom, a chlorine atom, a bromine atom, an iodine atom, an alkylsulfanyl group having from 1 to 4 carbon atoms, an alkylsulfonyl group having from 1 to 4 carbon atoms, an arylsulfonyl group having from 6 to 10 carbon atoms, a nitro group, a trifluoromethyl group and a cyano group, and preferred examples thereof include an acetyl group, a methoxycarbonyl group, a methylcarbamoyl group, an acetoxy group, an acetamide group, a methoxycarbonylamino group, a fluorine atom, a chlorine atom, a bromine atom, an iodine atom, a methylsulfanyl group, a phenylsulfonyl group, a nitro group, a trifluoromethyl group and a cyano group. The electron-donating substituent includes an alkyl group having from 1 to 4 carbon atoms, and preferred examples thereof include a methyl group, an ethyl group, a propyl group, an isopropyl group and a tert-butyl group. The substituent which is an electron-withdrawing group in the meta-position and an electron-donating group in the para- and ortho-positions includes an alkoxy group having from 1 to 4 carbon atoms, an aryl group having from 6 to 10 carbon atom and an aryloxy group having from 6 to 10 carbon atoms, and preferred examples thereof include a methoxy group, an ethoxy group, a propoxy group, an isopropoxy group, a tert-butoxy group, a phenyl group and a phenoxy group.

$Z^1$ in formula (3) or formula (4) of the aspect is a divalent spacer between $A^1$ and the hydrophilic polymer chain. It is composed of a covalent bond, is not particularly limited as long as it is more stable to hydrolysis than the acetal structure, and is preferably an ether bond, an ester bond, a carbonate bond, a urethane bond, an amide bond, a secondary amino group, an alkylene group containing any of these bonds and group, a single bond or an alkylene group. The number of carbon atoms of the alkylene group is preferably from 1 to 24.

By way of illustration and without limitation, preferred examples of the alkylene group include structures such as (z1) shown below. Preferred examples of the alkylene group having an ether bond include structures such as (z2) or (z3) shown below. Preferred examples of the alkylene group having an ester bond include structures such as (z4) shown below. Preferred examples of the alkylene group having a carbonate bond include structures such as (z5) shown below. Preferred examples of the alkylene group having a urethane bond include structures such as (z6) shown below. Preferred examples of the alkylene group having an amide bond include structures such as (z7) shown below. Preferred examples of the alkylene group having a secondary amino group include structures such as (z8) shown below. In a preferred embodiment, p and q are each independently an integer of 1 to 12. For example, in the case where the terminal active carbonate group is desired to be bonded in a hydrophobic environment, for example, the inside of a protein, p and q are preferably large, and in the case where it is desired to be bonded in a hydrophilic environment, p and q are preferably small. However, in the case where $Z^1$ is an ether bond, an ester bond, a carbonate bond, a urethane bond, an amide bond, a secondary amino group or an alkylene group containing any of these bonds and group and a plurality of identical structural units are connected, a number of the structural units described above is 2 or less.

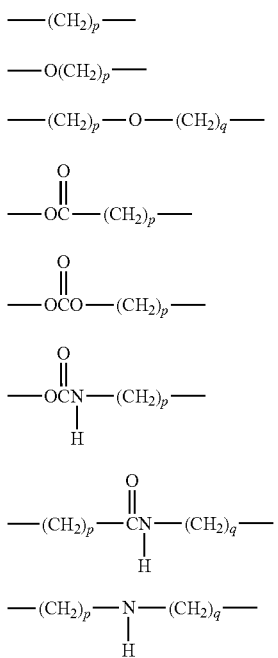

(z1)
(z2)
(z3)
(z4)
(z5)
(z6)
(z7)
(z8)

$E^1$ in formula (3) or formula (4) of the aspect is a leaving group and includes preferably a succinimidyloxy group, a phthalimidyloxy group, a 4-nitrophenoxy group, a 1-imidazolyl group, a pentafluorophenoxy group, a benzotriazol-1-yloxy group and a 7-azabenzotriazol-1-yloxy group, more preferably a succinimidyloxy group, a 4-nitrophenoxy group, a 1-imidazolyl group and a pentafluorophenoxy group, and still more preferably a succinimidyloxy group and a 4-nitrophenoxy group.

m in formula (3) or formula (4) of the aspect is 0 or 1. In a preferred embodiment, m is 0, and a hydrophilic polymer derivative represented by formula (20) or formula (21) is provided.

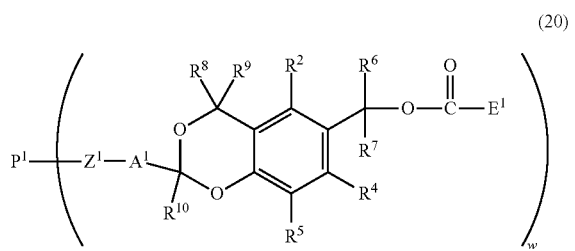

(20)

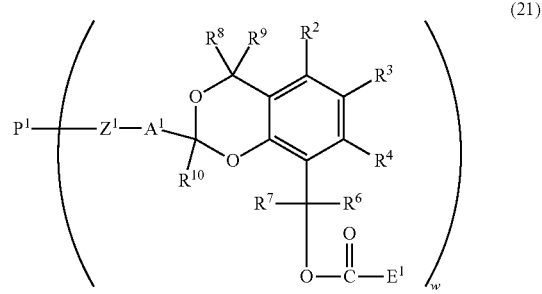

(21)

A degradation mechanism in a conjugate of the hydrophilic polymer derivative represented by formula (20) and a drug of the invention is described in the schematic diagram shown below.

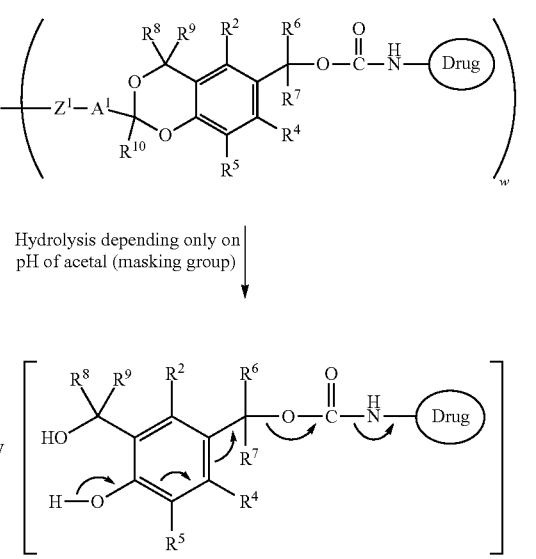

Hydrolysis depending only on pH of acetal (masking group)

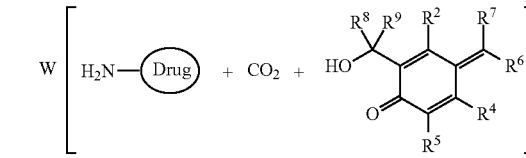

1,6-Benzyl elimination

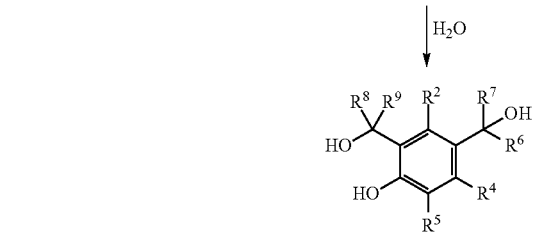

In another preferred embodiment of the aspect, m is 1 and $B^1$ is a hydrogen atom, and a hydrophilic polymer derivative represented by formula (22) or formula (23) is provided.

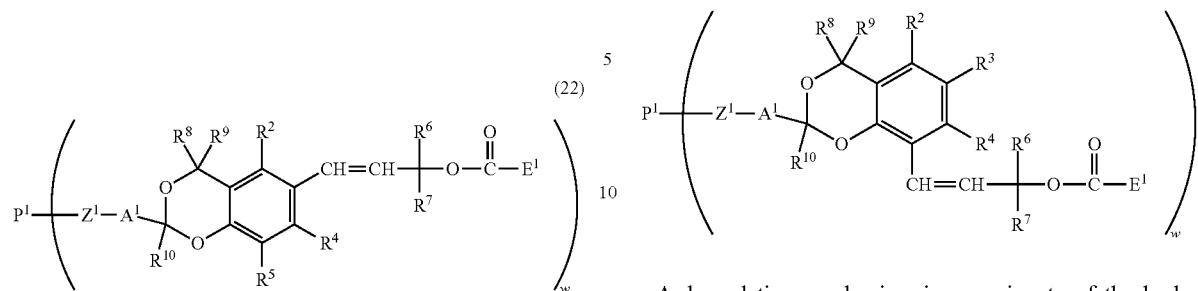
(22)
(23)
A degradation mechanism in a conjugate of the hydrophilic polymer derivative represented by formula (22) and a drug of the invention is described in the schematic diagram shown below.
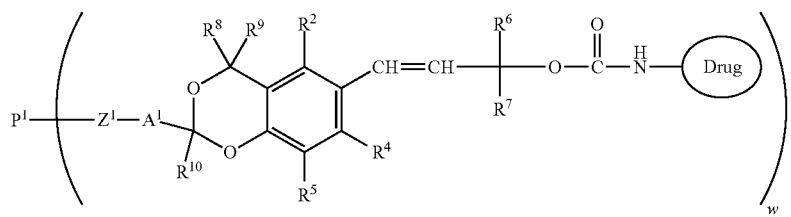
Hydrolysis depending only on pH of acetal (masking group)
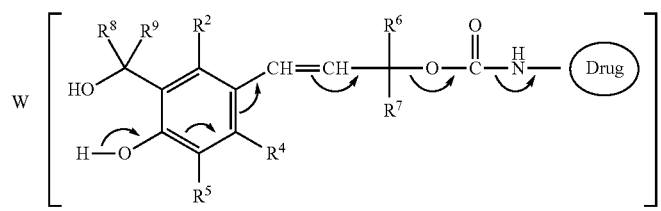
1,6-Benzyl elimination
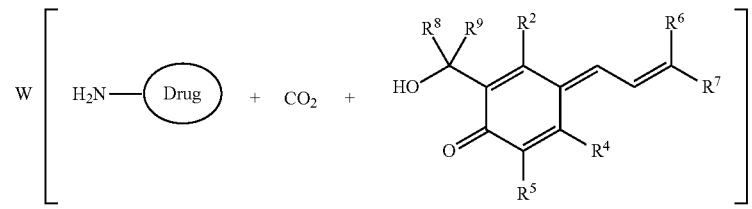
$H_2O$
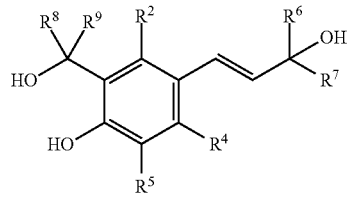

In still another preferred embodiment of the aspect, m is 1 and $B^1$ is —$C(R^6)(R^7)OC(O)E^1$, and a hydrophilic polymer derivative represented by formula (24) or formula (25) is provided. In the embodiment, two molecules of drugs can be pro-drugged with one molecule of the hydrophilic polymer derivative.

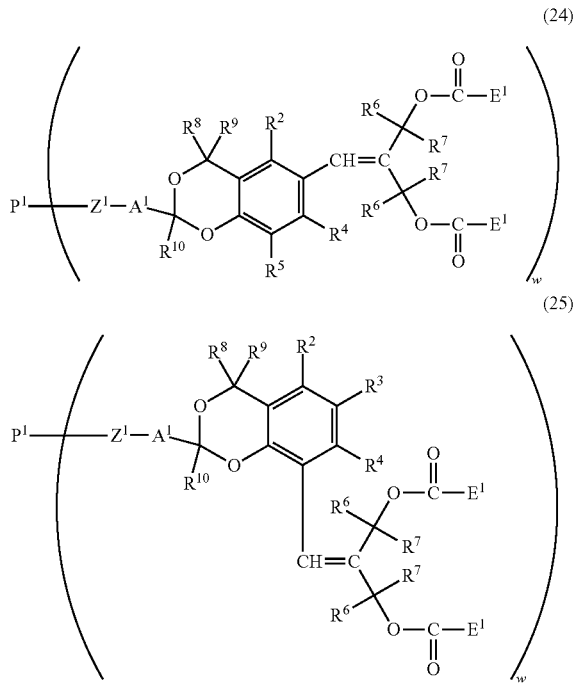

In another aspect of the invention, a hydrophilic polymer derivative represented by formula (5) or formula (6) is provided.

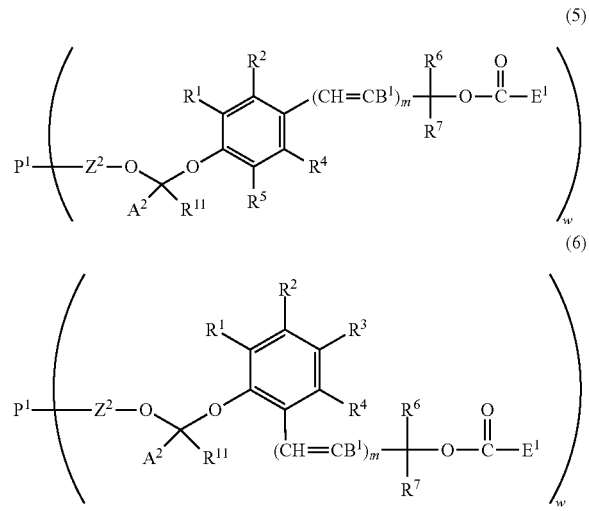

$R^1$, $R^2$, $R^3$, $R^4$, $R^5$, $R^6$, $R^7$ and $R^{11}$ in formula (5) or formula (6) of the aspect are each independently a hydrocarbon group having from 1 to 10 carbon atoms or a hydrogen atom. Specific examples of the hydrocarbon group of $R^1$, $R^2$, $R^3$, $R^4$, $R^5$, $R^6$, $R^7$ or $R^{11}$ include a methyl group, an ethyl group, a propyl group, an isopropyl group, a tert-butyl group, a phenyl group and a benzyl group. A preferred embodiment of $R^1$, $R^2$, $R^3$, $R^4$, $R^5$, $R^6$, $R^7$ or $R^1$ is a hydrogen atom or a methyl group, and more preferably a hydrogen atom.

$A^2$ in formula (5) or formula (6) of the aspect is a hydrocarbon group having from 1 to 10 carbon atoms, a phenyl group which may have a substituent or a hydrogen atom, and is preferably a hydrocarbon group having from 1 to 10 carbon atoms or a phenyl group which may have a substituent.

Specific examples of the hydrocarbon group include a methyl group, an ethyl group, a propyl group, an isopropyl group and a tert-butyl group. The substituent for the phenyl group may be any of an electron-withdrawing substituent and an electron-donating substituent and may be used individually or in combination as long as the substituent does not cause a side reaction in the synthesis process of the hydrophilic polymer derivative. The electron-withdrawing substituent includes an acyl group having from 2 to 5 carbon atoms, an alkoxycarbonyl group having from 2 to 5 carbon atoms, a carbamoyl group having from 2 to 5 carbon atoms, an acyloxy group having from 2 to 5 carbon atoms, an acylamino group having from 2 to 5 carbon atoms, an alkoxycarbonylamino group having from 2 to 5 carbon atoms, a fluorine atom, a chlorine atom, a bromine atom, an iodine atom, an alkylsulfanyl group having from 1 to 4 carbon atoms, an alkylsulfonyl group having from 1 to 4 carbon atoms, an arylsulfonyl group having from 6 to 10 carbon atoms, a nitro group, a trifluoromethyl group and a cyano group, and preferred examples thereof include an acetyl group, a methoxycarbonyl group, a methylcarbamoyl group, an acetoxy group, an acetamide group, a methoxycarbonylamino group, a fluorine atom, a chlorine atom, a bromine atom, an iodine atom, a methylsulfanyl group, a phenylsulfonyl group, a nitro group, a trifluoromethyl group and a cyano group. The electron-donating substituent includes an alkyl group having from 1 to 4 carbon atoms, and preferred examples thereof include a methyl group, an ethyl group, a propyl group, an isopropyl group and a tert-butyl group. The substituent which is an electron-withdrawing group in the meta-position and an electron-donating group in the para- and ortho-positions includes an alkoxy group having from 1 to 4 carbon atoms, an aryl group having from 6 to 10 carbon atom and an aryloxy group having from 6 to 10 carbon atoms, and preferred examples thereof include a methoxy group, an ethoxy group, a propoxy group, an isopropoxy group, a tert-butoxy group, a phenyl group and a phenoxy group.

$Z^2$ in formula (5) or formula (6) of the aspect is a divalent spacer between one oxygen atom of the acetal and the hydrophilic polymer chain. It is composed of a covalent bond, is not particularly limited as long as it is more stable to hydrolysis than the acetal structure, and is preferably an ether bond, an ester bond, a carbonate bond, a urethane bond, an amide bond, a secondary amino group, an alkylene group containing any of these bonds and group, a single bond or an alkylene group. The number of carbon atoms of the alkylene group is preferably from 1 to 24.

By way of illustration and without limitation, preferred examples of the alkylene group include structures such as (z1) shown below. Preferred examples of the alkylene group having an ether bond include structures such as (z2) or (z3) shown below. Preferred examples of the alkylene group having an ester bond include structures such as (z4) shown below. Preferred examples of the alkylene group having a carbonate bond include structures such as (z5) shown below. Preferred examples of the alkylene group having a urethane bond include structures such as (z6) shown below. Preferred examples of the alkylene group having an amide bond include structures such as (z7) shown below. Preferred examples of the alkylene group having a secondary amino group include structures such as (z8) shown below. In a preferred embodiment, p and q are each independently an integer of 1 to 12. For example, in the case where the terminal active carbonate group is desired to be bonded in a hydrophobic environment, for example, the inside of a protein, p and q are preferably large, and in the case where it is desired to be bonded in a hydrophilic environment, p and q are preferably small. However, in the case where $Z^2$ is an ether bond, an ester bond, a carbonate bond, a urethane bond, an amide bond, a secondary amino group or an alkylene group containing any of these bonds and group and a plurality of identical structural units are connected, a number of the structural units described above is 2 or less.

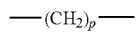 (z1)

 (z2)

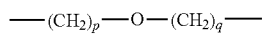 (z3)

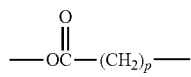 (z4)

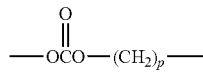 (z5)

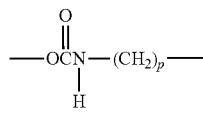 (z6)

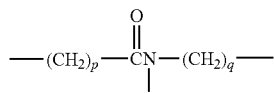 (z7)

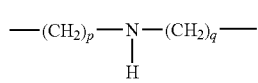 (z8)

$E^1$ in formula (5) or formula (6) of the aspect is a leaving group and includes preferably a succinimidyloxy group, a phthalimidyloxy group, a 4-nitrophenoxy group, a 1-imidazolyl group, a pentafluorophenoxy group, a benzotriazol-1-yloxy group and a 7-azabenzotriazol-1-yloxy group, more preferably a succinimidyloxy group, a 4-nitrophenoxy group, a 1-imidazolyl group and a pentafluorophenoxy group, and still more preferably a succinimidyloxy group and a 4-nitrophenoxy group.

m in formula (5) or formula (6) of the aspect is 0 or 1. In a preferred embodiment, m is 0, and a hydrophilic polymer derivative represented by formula (26) or formula (27) is provided.

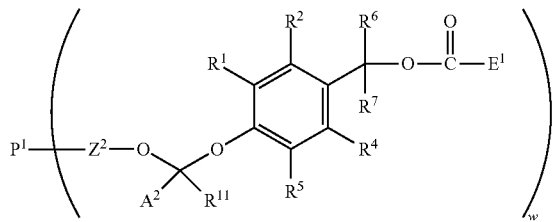 (26)

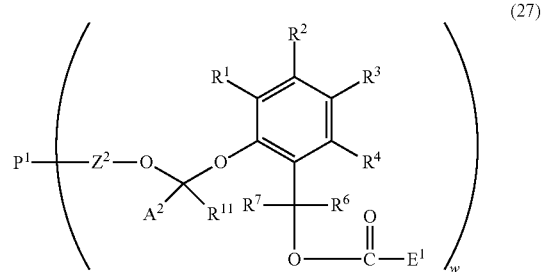 (27)

In another preferred embodiment of the aspect, m is 1 and $B^1$ is a hydrogen atom, and a hydrophilic polymer derivative represented by formula (28) or formula (29) is provided.

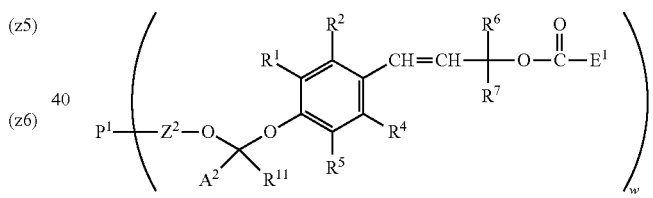 (28)

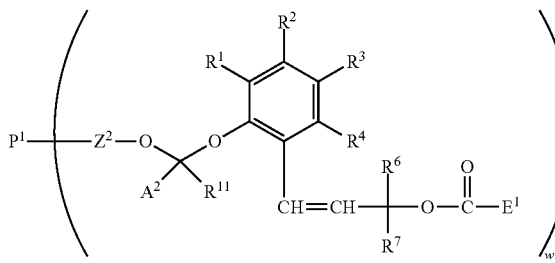 (29)

In still another preferred embodiment of the aspect, m is 1 and $B^1$ is —C($R^6$)($R^7$)OC(O)$E^1$, and a hydrophilic polymer derivative represented by formula (30) or formula (31) is provided. In the embodiment, a derivative having two $E^1$ with respect to one acetal is provided.

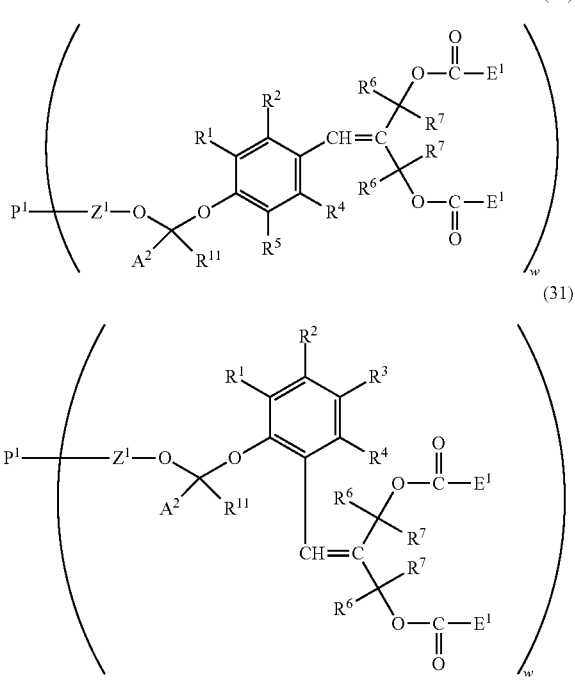

In one aspect of the invention, $P^1$ in formula (3), formula (4), formula (5) or formula (6) is a straight-chain polyethylene glycol.

In a preferred embodiment of the aspect, $P^1$ in formula (3), formula (4), formula (5) or formula (6) is represented by formula (7).

$$Y^1-(OCH_2CH_2)_n- \qquad (7)$$

In the formula, n is a number of repeating units per polyethylene glycol chain, and in the polyethylene glycol having a molecular weight distribution, it is defined that n is calculated by various theoretical calculations based on a number average molecular weight (Mn) of the compound.

In the formula, $Y^1$ is a hydrocarbon group having from 1 to 24 carbon atoms, specific examples thereof include a methyl group, an ethyl group, a propyl group, an isopropyl group, a butyl group, a tert-butyl group, a pentyl group, an isopentyl group, a hexyl group, a heptyl group, a 2-ethylhexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a heneicosyl group, a docosyl group, a toicosyl group, a tetracosyl group, a phenyl group, a benzyl group, a cresyl group, a butylphenyl group, a dodecylphenyl group and a trityl group, and $Y^1$ is preferably a hydrocarbon group having from 1 to 10 carbon atoms, more preferably a methyl group or an ethyl group, and still more preferably a methyl group.

In another preferred embodiment of the aspect, $P^1$ in formula (3), formula (4), formula (5) or formula (6) is represented by formula (8).

$$X^1-Z^3-(OCH_2CH_2)_n- \qquad (8)$$

In the formula, $X^1$ is a chemically reactive functional group, and $Z^3$ is a divalent spacer between the functional group $X^1$ and the polyethylene glycol chain.

The polyethylene glycol derivative of the embodiment is able to provide a drug conjugate having a target-directing performance, for example, by connecting a drug to an active carbonate group and connecting a biofunctional molecule having a target-directing property, for example, an antibody, to $X^1$.

Preferred examples of $X^1$ include an aldehyde group, an epoxy group, a maleimide group, a vinyl sulfone group, an acryl group, a sulfonyloxy group, a carboxy group, a thiol group protected by a protective group, a dithiopyridyl group, an α-haloacetyl group, an alkynyl group, an allyl group, a vinyl group, an amino group protected by a protective group, an oxyamino group protected by a protective group, a hydrazide group protected by a protective group and an azide group.

More specifically, the functional group capable of forming a covalent bond upon a reaction with an amino group of the biofunctional molecule is an aldehyde group, an epoxy group, a maleimide group, a vinyl sulfone group, an acryl group, a sulfonyloxy group or a carboxy group, the functional group capable of forming a covalent bond upon a reaction with a thiol group of the biofunctional molecule is an aldehyde group, an epoxy group, a maleimide group, a vinyl sulfone group, an acryl group, a sulfonyloxy group, a carboxy group, a thiol group protected by a protective group, a dithiopyridyl group, an α-haloacetyl group, an alkynyl group, an allyl group or a vinyl group, the functional group capable of forming a covalent bond upon a reaction with an aldehyde group or a carboxy group of the biofunctional molecule is a thiol group protected by a protective group, an amino group protected by a protective group, an oxyamino group protected by a protective group or a hydrazide group protected by a protective group, the functional group capable of forming a covalent bond upon a reaction with an alkynyl group of the biofunctional molecule is a thiol group protected by a protective group or an azide group, and the functional group capable of forming a covalent bond upon a reaction with an azide group of the biofunctional molecule is an alkynyl group or a functional group containing a triple bond.

The "protective group" as referred to herein is a component which prevents or blocks a reaction of a specific chemically reactive functional group in the molecule under certain reaction conditions. The protective group varies depending on the kind of the chemically reactive functional group to be protected, the conditions to be used and the presence of the other functional group or protective group in the molecule. Specific examples of the protective group can be found in many general books and are described, for example, in "Wuts, P. G M.; Greene, T. W., Protective Groups in Organic Synthesis, 4th ed.; Wiley-Interscience: New York, 2007". Moreover, the functional group protected by the protective group can reproduce the original functional group by deprotection using reaction conditions suitable for each of the protective groups, that is, causing a chemical reaction. Therefore, in the specification, a functional group which is protected by a protective group and is capable of being deprotected by various reactions is included in the "chemically reactive functional group". The typical deprotection conditions of the protective group are described in the literature described above.

As to preferred combinations of the functional group to be protected and the protective group, when the functional group to be protected is an amino group, for example, an acyl protective group and a carbamate protective group are exemplified, and specific examples thereof include a trifluoroacetyl group, a 9-fluorenylmethyloxycarbonyl group and a 2-(trimethylsilyl)ethyloxycarbonyl group. When the functional group to be protected is a hydroxy group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group. When the functional group to be protected is a carboxy group, for example, an alkyl ester protective group and a silyl ester protective group are exemplified, and specific examples thereof include a methyl group, a 9-fluorenylmethyl group and a tert-butyldimethylsilyl group. When the functional group to be protected is a sulfanyl group, for example, an acyl protective group, a thioether protective group, a thiocarbonate protective group and a disulfide protective group are exemplified, and specific examples thereof include an S-2,4-dinotrophenyl group, an S-9-fluorenylmethyloxycarbonyl group and an S-tert-butyldisulfide group. The typical deprotection conditions of the protective group are described in the literature described above, and the reaction conditions suitable for each of the protective groups can be selected.

In a preferred embodiment of the aspect, $X^1$ is a group represented by group (I), group (II), group (III), group (IV) or group (V).

Group (I): Functional group capable of forming a covalent bond upon a reaction with an amino group of the biofunctional molecule
 (a), (b), (e) and (f) shown below;
Group (II): Functional group capable of forming a covalent bond upon a reaction with a thiol group of the biofunctional molecule
 (a), (b), (c), (d), (e), (f) and (l) shown below;
Group (III): Functional group capable of forming a covalent bond upon a reaction with an aldehyde group or a carboxy group of the biofunctional molecule
 (g), (h), (i), (j) and (o) shown below;
Group (IV): Functional group capable of forming a covalent bond upon a reaction with an alkynyl group of the biofunctional molecule
 (c), (d), (g), (h), (i), (j) and (k) shown below;
Group (V): Functional group capable of forming a covalent bond upon a reaction with an azide group of the biofunctional molecule
 (m) and (n) shown below.

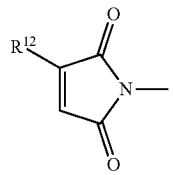
(a)

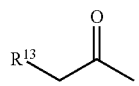
(b)

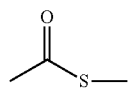
(c)

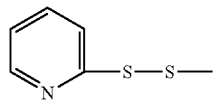
(d)

(e)

HOOC— (f)

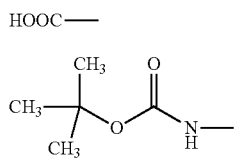
(g)

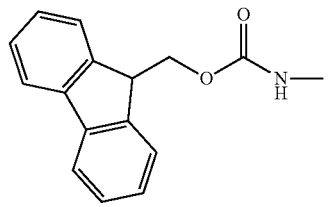
(h)

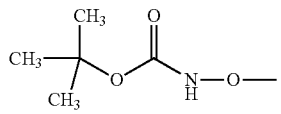
(i)

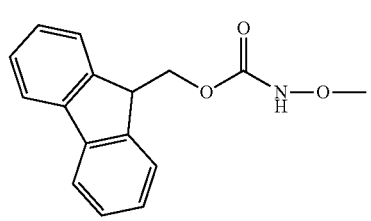
(j)

 N₃— (k)

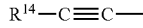 R¹⁴—C≡C— (l)

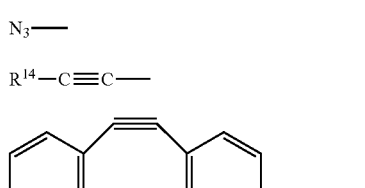
(m)

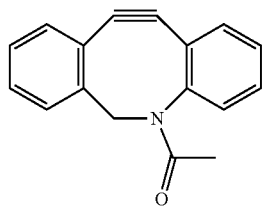
(n)

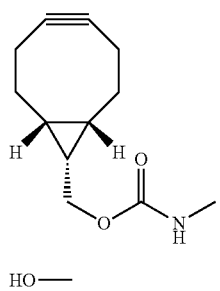

HO— (o)

In the formulae above, $R^{12}$ and $R^{14}$ are each a hydrogen atom or a hydrocarbon group having from 1 to 5 carbon atoms, and specific examples of the hydrocarbon group include a methyl group, an ethyl group, a propyl group, an isopropyl group, a butyl group, a tert-butyl group and a pentyl group. $R^{13}$ is a halogen atom selected from a chlorine atom, a bromine atom and an iodine atom.

$Z^3$ is composed of a covalent bond, is not particularly limited as long as it is more stable to hydrolysis than the acetal structure, and is preferably an ether bond, an ester bond, a carbonate bond, a urethane bond, an amide bond, a secondary amino group, an alkylene group containing any of these bonds and group, a single bond or an alkylene group.

The number of carbon atoms of the alkylene group is preferably from 1 to 24. By way of illustration and without limitation, preferred examples of the alkylene group include structures such as (z1) shown below. Preferred examples of the alkylene group having an ether bond include structures such as (z2) or (z3) shown below. Preferred examples of the alkylene group having an ester bond include structures such as (z4) shown below.

Preferred examples of the alkylene group having a carbonate bond include structures such as (z5) shown below. Preferred examples of the alkylene group having a urethane bond include structures such as (z6) shown below. Preferred examples of the alkylene group having an amide bond include structures such as (z7) shown below. Preferred examples of the alkylene group having a secondary amino group include structures such as (z8) shown below. In a preferred embodiment, p and q are each independently an integer of 1 to 12. For example, in the case where the functional group $X^1$ is desired to be bonded in a hydrophobic environment, for example, the inside of a protein, p and q are preferably large, and in the case where it is desired to be bonded in a hydrophilic environment, p and q are preferably small. However, in the case where $Z^3$ is an ether bond, an ester bond, a carbonate bond, a urethane bond, an amide bond, a secondary amino group or an alkylene group containing any of these bonds and group and a plurality of identical structural units are connected, a number of the structural units described above is 2 or less.

 (z1)

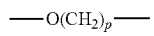 (z2)

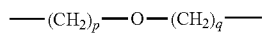 (z3)

(z4)

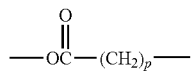 (z5)

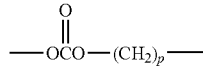 (z6)

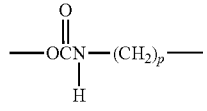 (z7)

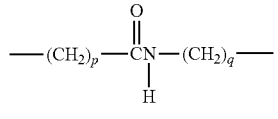 (z8)

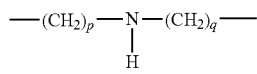

In another aspect of the invention, $P^1$ in formula (3), formula (4), formula (5) or formula (6) is a branched polyethylene glycol.

In a preferred embodiment of the aspect, $P^1$ in formula (3), formula (4), formula (5) or formula (6) is represented by formula (9).

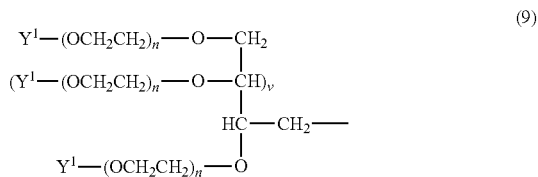

(9)

In the formula, $Y^1$ is a hydrocarbon group having from 1 to 24 carbon atoms as described above, and v is 0 or 2.

In the case where v is 0, two polyethylene glycol chains are present and, in the case where v is 2, four polyethylene glycol chains are present. In general, in the chemical modification of a bio-related substance with polyethylene glycol, when connecting points to the polyethylene glycol are introduced more than necessary, the active sites of the bio-related substance are destroyed to reduce its function so that an attempt to increase the effect by increasing a molecular weight of the polyethylene glycol has been performed. However, the viscosity increases with the increase in the molecular weight and hence, for example, handling as an aqueous solution preparation, for example, an injection preparation becomes difficult. Since the polyethylene glycol derivative has a branched structure, it shows low viscosity in comparison with a straight-chain polyethylene glycol derivative having the same molecular weight, and thus it is useful in application, for example, the aqueous solution preparation.

In another preferred embodiment of the aspect, $P^1$ in formula (3), formula (4), formula (5) or formula (6) is represented by formula (10).

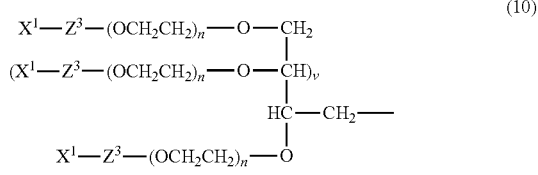

(10)

In the formula, $X^1$ is a chemically reactive functional group as described above, $Z^3$ is a divalent spacer as described above, and v is 0 or 2.

The polyethylene glycol derivative of the embodiment has one active carbonate group and two or four $X^1$ and is able to provide a drug conjugate having a high target-directing performance, for example, by connecting a drug to the active carbonate group and connecting a biofunctional molecule having a target-directing property, for example, an antibody, to $X^1$.

In still another preferred embodiment of the aspect, $P^1$ in formula (3), formula (4), formula (5) or formula (6) is represented by formula (11).

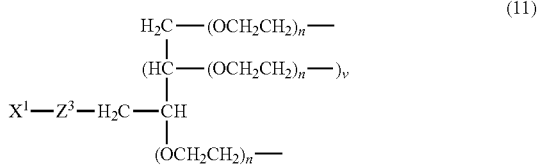

(11)

In the formula, $X^1$ is a chemically reactive functional group as described above, $Z^3$ is a divalent spacer as described above, and v is 0 or 2.

In the antibody-drug conjugate (ADC)-related field, in order to increase drug transportation efficiency, it is preferred to connect a plurality of drugs to an antibody, but when a plurality of connecting points are introduced into the antibody, a problem arises in that the affinity to an antigen is decreased. The polyethylene glycol derivative of the embodiment has two or four active carbonate groups and one $X^1$ and, for example, when an anticancer agent is connected to the active carbonate group and an antibody is connected to $X^1$ in ADC targeting cancer, it is possible to improve the transportation efficiency of the anticancer agent without increasing the connecting points to the antibody.

In still another aspect of the invention, $P^1$ in formula (3), formula (4), formula (5) or formula (6) is polyethylene glycol having the number of terminals of 2 to 8, all the terminals of the polyethylene glycol constituting $P^1$ are each connected to $Z^1$ in formula (3) or formula (4) or $Z^2$ in formula (5) or formula (6), and w is equal to the number of terminals of the polyethylene glycol.

In a preferred embodiment of the aspect, $P^1$ in formula (3), formula (4), formula (5) or formula (6) is selected from the group consisting of formula (r), formula (s), formula (t), formula (u) and formula (v), w is 2 in the case where $P^1$ is represented by formula (r), w is 3 in the case where $P^1$ is represented by formula (s), w is 4 in the case where $P^1$ is represented by formula (t), w is 4 in the case where $P^1$ is represented by formula (u), and w is 8 in the case where $P^1$ is represented by formula (v).

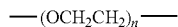
(r)

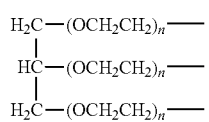
(s)

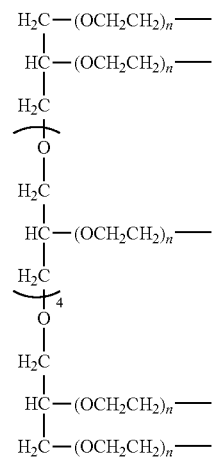
(t)

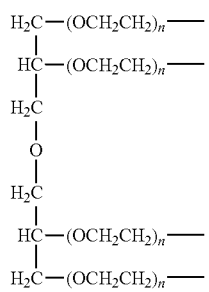
(u)

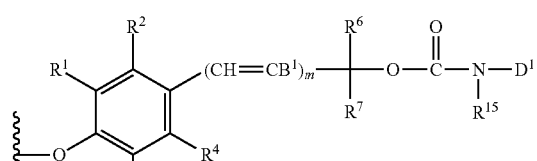
(v)

A preferred range of n in formula (7) or formula (8) of the invention is from 3 to 2,000, more preferably from 20 to 1,500, still more preferably from 40 to 1,000, and most preferably from 60 to 500. A preferred range of n in formula (9), formula (10) or formula (11) is from 3 to 1,000, more preferably from 10 to 800, still more preferably from 20 to 500, and most preferably from 30 to 300. Further, a preferred range of n in formula (r), formula (s), formula (t), formula (u) or formula (v) is from 3 to 2,000, more preferably from 20 to 1,500, still more preferably from 40 to 1,000, and most preferably from 60 to 500.

In still another aspect of the invention, a conjugate having a structure represented by formula (12) or formula (13) obtained by reacting the active carbonate group of the hydrophilic polymer derivative having a self-immolative acetal linker according to the invention with an amino group contained in a biofunctional molecule is provided.

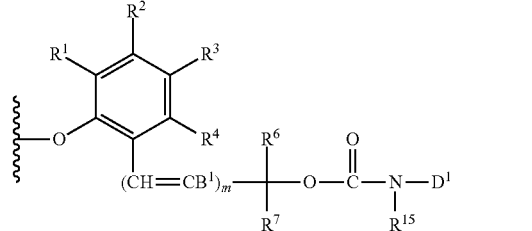

$D^1$ in formula (12) or formula (13) of the aspect is a residue obtained by eliminating an amino group which is reacted with the active carbonate group of the hydrophilic polymer derivative having a self-immolative acetal linker according to the invention to constitute a carbamate bond among the amino groups contained in a biofunctional molecule. $R^{15}$ is a substituent of the amino group and is a hydrocarbon group having from 1 to 10 carbon atoms or a hydrogen atom. Specific examples of the hydrocarbon group include a methyl group, an ethyl group, a propyl group, an isopropyl group, a tert-butyl group, a phenyl group and a benzyl group. A preferred embodiment of $R^{15}$ is a hydrogen atom or a methyl group, and more preferably a hydrogen atom.

In a preferred embodiment of the aspect, the biofunctional molecule includes a chemotherapeutic agent. The chemotherapeutic agent is a compound useful in the treatment of cancer. Examples of the chemotherapeutic agent include the followings: alkylating agents, for example, thiotepa or cyclophosphamide (CYTOXAN (trademark)); alkyl sulfonates, for example, busulfan, improsulfan or piposulfan; aziridines for example, benzodopa, carboquone, meturedopa or uredopa; ethyleneimines and methylamelamines including altretamine, triethylenemelamine, triethylenephosphoramide, triethylenethiophosphoramide and trimethylolomelamine; acetogenins (particularly bullatacin and bullatacinone); camptothecin (including synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including synthetic analogs KW-2189 and CBI-TMI; eleutherobin; pancratistatin; sarcodictyin; spongistatin; nitrogen mustards, for example, chlorambucil, chlornaphazine, cholophosphamide, estramustine, ifosfamide, mechlorethamine, mechlorethamine oxide hydrochloride, melphalan, novembichin, phenesterine, prednimustine, trofosfamide or uracil mustard; nitrosoureas, for example, carmustine, chlorozotocin, fotemustine, lomustine, nimustine or ranimustine; antibiotics, for example, enediyne antibiotics (for example, calicheamicin, particularly calicheamicin gamma 1 and calicheamicin theta 1, see, for example, Angew Chem Intl. Ed. Engl. 33:183-186 (1994); dynemicin (including dynemicin A); esperamicin; or neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, for example, methotrexate or 5-fluorouracil (5-FU); folic acid analogs, for example, demopterin, methotrexate, pteropterin or trimetrexate; purine analogs, for example, fludarabine, 6-mercaptopurine, thiamiprine or thioguanine; pyrimidine analogs, for example, ancitabine, azacitidine, 6-azauridine, carmofur, cytarabine, dideoxyuridine, doxifluridine, enocitabine, floxuridine or 5-FU; androgens, for example, calusterone, dromostanolone propionate, epitiostanol, mepitiostane or testolactone; anti-adrenals, for example, aminoglutethimide, mitotane or trilostane; folic acid replenisher, for example, frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; epothilone; etogiucid; gallium nitrate; hydroxy urea; lentinan; lonidamine; maytansinoids, for example, maytansine or ansamitocins; mitoguazone; mitoxantrone; mopidamol; nitracrine; pentostatin; phenamet; pirarubicin; podophyllinic acid; 2-ethylhydrazide; procarbazine; PSK (registered trademark); razoxane; rhizoxin; sizofiran; spirogermanium; tenuazonic acid; triaziquone; 2,2',2''-trichlorotriethylamine; trichothecenes (particularly T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiotepa; taxoids, for example, paclitaxel (TAXOL (registered trademark), Bristol-Myers Squibb Oncology) or doxetaxel (TAXOTERE (registered trademark), Rhone-Poulenc Rorer); chlorambucil; gemcitabine; 6-thioguanine; mercaptopurine; methotrexate; platinum analogs, for example, cisplatin or carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of those described above. Anti-hormonal agents which act to regulate or inhibit hormone action on tumors, for example, anti-estrogen drugs including, for example, tamoxifen, raloxifene, 4(5)-imidazoles inhibiting aromatase, 4-hydroxytamoxifen, trioxifene, keoxifene, LY 117018, onapristone and toremifene (Fareston); and anti-androgen drugs, for example, flutamide, nilutamide, bicalutamide, leuprolide or goserelin; siRNA, and pharmaceutically acceptable salts, acids or derivatives of any of those described above are also included in the definition.

Other chemotherapeutic agents which can be used with the invention are disclosed in U.S. Patent Application Publication Nos. 2008/0171040 and 2008/0305044, all of which are incorporated by reference in their entirety herein.

In a preferred embodiment of the invention, the chemotherapeutic agent is a low molecular drug. The low molecular drug has a molecular weight preferably from 100 to 1,500, more preferably from 120 to 1,200, and still more preferably from 200 to 1,000. Typically, as the low molecular drug, organic, inorganic or organometallic compounds having a molecular weight of less than about 1,000 is widely used. The low molecular drugs of the invention also include oligopeptides and other biomolecules each having a molecular weight of less than about 1,000. The low molecular drugs are well characterized in the art, for example, especially in WO 05/058367, EP-A-85901495, EP-A-8590319 and U.S. Pat. No. 4,956,303, all of which are incorporated by reference in their entirety herein.

A preferred low molecular drug of the invention is a low molecular drug capable of being linked to the antibody. The invention includes known drugs as well as those which may become known. Particularly preferred low molecular drugs include a cytotoxic agent.

Preferred cytotoxic agents include maytansinoids, CC-1065 analogues, morpholinos, doxorubicins, taxanes, crtptophycins, epothilones, calicheamicins, auristatins and pyrrolobenzodiazepine dimers.

The term "antibody" as used in the specification is used in its broadest sense and specifically covers a monoclonal antibody, a polyclonal antibody, a dimer, a multimer, a multispecific antibody (for example, a bispecific antibody) and an antibody fragment, as far as it exhibits the desired biological activity (Miller, K. et al. J. Immunol. 2003, 170, 4854-4861). The antibody can be a mouse antibody, a human antibody, a humanized antibody or a chimeric antibody, or can be derived from other species. The antibody is a protein generated by the immune system, which is capable of recognizing and binding to a specific antigen (Janeway, C.; Travers, P.; Walport, M.; Shlomchik, M. Immunobiology, 5th ed.; Garland Publishing: New York, 2001). A target antigen generally has numerous binding sites (also called epitopes) recognized by CDRs on multiple antibodies. An antibody which specifically binds to a different epitope has a different structure. Therefore, one antigen may have more than one corresponding antibody. The antibody includes the full-length immunoglobulin molecule or an immunologically active portion of a full-length immunoglobulin molecule (that is, a molecule containing an antigen binding site which immunospecifically binds to an antigen of interest or part thereof). Such a target includes a cancer cell and a cell which generates an autoimmune antibody associated with an autoimmune disease, but it is not limited thereto. The immunoglobulin disclosed in the specification may be of any type (for example, IgG, IgE, IgM, IgD or IgA), class (for example, IgG1, IgG2, IgG3, IgG4, IgA1 or IgA2) or subclass thereof. The immunoglobulin may be derived from any species. However, in one embodiment, the immunoglobulin is of human origin, mouse origin or rabbit origin.

The polyclonal antibody is a heterogeneous population of antibody molecules, for example, that derived from the serum of immunized animal. The polyclonal antibody to an antigen of interest may be produced using known various procedures in the art. For example, in order to produce a polyclonal antibody, various host animals including, but not limited to, rabbit, mouse, rat and guinea pig, may be immunized by injection with an antigen of interest or derivative thereof. The immunological response may be increased by using various adjuvants including, but not limited to, Freund's (complete and incomplete) adjuvant, a mineral gel, for example, aluminum hydroxide, a surface active substance, for example, lysolecithin, a pluronic polyol, a polyanion, a peptide, an oil emulsion, keyhole limpet hemocyanin, dinitrophenol, and a potentially useful human adjuvant, for example, BCG (Bacille Calmett-Guerin) or *Corynebacterium parvum*, depending on the host species. Such adjuvants are also known in the art.

The monoclonal antibody is a homogeneous population of antibodies to a specific antigenic determinant (for example, a cell antigen (cancer or autoimmune cell antigen), a viral antigen, a microbial antigen, a protein, a peptide, a carbohydrate, a chemical substance, a nucleic acid or antigen-binding fragments thereof). A monoclonal antibody (mAb) to an antigen of interest may be prepared by using any technique known in the art. These include, but are not limited to, the hybridoma technique originally described by Kohler, G; Milstein, C. Nature 1975, 256, 495-497, the human B cell hybridoma technique (Kozbor, D. et al. Immunol. Today 1983, 4, 72-79) and the EBV-hybridoma technique (Cole, S. P. C. et al. Monoclonal Antibodies and Cancer Therapy; Alan R. Liss: New York, 1985, pp. 77-96). Such antibodies may be of any immunoglobulin class including IgG, IgM, IgE, IgA and IgD and any subclass thereof. The hybridoma producing the monoclonal antibody in the invention may be cultivated in vitro or in vivo.

The monoclonal antibody includes, but is not limited to, a human monoclonal antibody, a humanized monoclonal antibody, a chimeric monoclonal antibody and an antibody fragment. The human monoclonal antibody may be made by any of numerous techniques known in the art (see, for example, Teng, N. N. et al. Proc. Natl. Acad. Sci. USA. 1983, 80, 7308-7312, Kozbor, D. et al. Immunology Today 1983, 4, 72-79, Olsson L. et al. Meth. Enzymol. 1982, 92, 3-16, and U.S. Pat. Nos. 5,939,598 and 5,770,429). A recombinant antibody, for example, a chimeric monoclonal antibody or a humanized monoclonal antibody can be made using standard recombinant DNA techniques known in the art (see, for example, U.S. Pat. Nos. 4,816,567 and 4,816,397).

The immunogenicity of the antibody can also be reduced by the surface reconstruction (resurfacing) treatment of the antibody (see, U.S. Pat. No. 5,225,539 and European Patents 0239400, 0519596 and 0592106).

In one embodiment of the invention, the antibody may be a bispecific antibody. Methods for making the bispecific antibody are known in the art. Conventional production method of full-length bispecific antibody utilizes the simultaneous expression of two immunoglobulin heavy chain-light chain pairs in which the two chains have different specificities (see, Milstein, C. et al. Nature 1983, 305, 537-539). According to a different method, the bispecific antibody can also be produced by fusing an antibody variable domain with the desired binding specificity (antibody-antigen binding site) to an immunoglobulin constant domain sequence.

Other useful antibodies include fragments of antibodies, but are not limited to, F(ab')2 fragment, Fab' fragment, Fab fragment, Fvs, a single chain antibody (SCA) (for example, as described in U.S. Pat. No. 4,946,778, Bird, R. E. et al. Science 1988, 242, 423-442, Huston, J. S. et al. Proc. Natl. Acad. Sot USA 1988, 85, 5879-5883, and Ward, E. S. et al. Nature 1989, 334, 544-554), scFv, sc-Fv-Fc, FvdsFv, minibody, diabody, triabody, tetrabody, and any other molecule containing CDR and having the same specificity as the antibody, for example, a domain antibody.

In a preferred embodiment of the invention, a known antibody for the treatment or prevention of cancer may be used. All target proteins including any target protein whose expression is correlated with expression on cells of a cancer, cell proliferative disorder or tumor can be targeted by an antibody.

In a preferred embodiment of the invention, the antibody is useful for the treatment of cancer. Examples of the antibody useful for the treatment of cancer include, but are not limited to, RITUXAN (registered trademark) (Genentech Inc.) which is a chimeric anti-CD20 monoclonal antibody for the treatment of patient with non-Hodgkin's lymphoma, OVAREX (AltaRex Corp.) which is a mouse antibody for the treatment of ovarian cancer, PANOREX (Glaxo Wellcome Inc.) which is a mouse IgG2a antibody for the treatment of colorectal cancer, CETUXIMAB ERBITUX (ImClone Systems Inc.) which is an anti-EGFR IgG chimeric antibody for the treatment of epidermal growth factor positive cancer, for example, head cancer or neck cancer, VITAXIN (MedImmune Inc.) which is a humanized antibody for the treatment of sarcoma, CAMPATH I/H (Leukosite Inc.) which is a humanized IgG1 antibody for the treatment of chronic lymphocytic leukemia (CLL), Smart M195 (Protein Design Labs Inc.) which is a humanized anti-CD33 IgG antibody for the treatment of acute myeloid leukemia (AML), LYMPHOCIDE (Immunomedics Inc.) which is a humanized anti-CD22 IgG antibody for the treatment of non-Hodgkin's lymphoma, Smart ID10 (Protein Design Labs Inc.) which is a humanized anti-HLA-DR antibody for the treatment of non-Hodgkin's lymphoma, Oncolym (Techniclone Inc.) which is a radiolabeled mouse anti-HLA-Dr10 antibody for the treatment of non-Hodgkin's lymphoma, ALLOMUNE (BioTransplant Inc.) which is a humanized anti-CD2 mAb for the treatment of Hodgkin's disease or non-Hodgkin's lymphoma, AVASTIN (Genentech Inc.) which is an anti-VEGF humanized antibody for the treatment of lung cancer and colorectal cancer, Epratuzamab (Immunomedics Inc. and Amgen Inc.) which is an anti-CD22 antibody for the treatment of non-Hodgkin's lymphoma, and CEAcide (Immunomedics Inc.) which is a humanized anti-CEA antibody for the treatment of colorectal cancer.

In a preferred embodiment of the invention, the antibody is an antibody to the following antigens: CA125, CA15-3, CA19-9, L6, Lewis Y, Lewis X, alpha fetoprotein, CA242, placental alkaline phosphatase, prostate specific membrane antigen, EphB2, TMEFF2, prostatic acid phosphatase, epidermal growth factor, MAGE-1, MAGE-2, MAGE-3, MAGE-4, anti-transferrin receptor, p97, MUC1-KLH, CEA, gp 100, MART 1, prostate specific antigen, IL-2 receptor, CD20, CD52, CD33, CD22, human chorionic gonadotropin, CD38, CD40, mucin, P21, MPG and Neu oncogene product. Some specific useful antibodies include, but are not limited to, mAb to the CD40 antigen, for example, BR96 mAb (Trail, P. A. et al. Science 1993, 261, 212-215), BR64 (Trail, P. A. et al. Cancer Research 1997, 57, 100-105) or S2C6 mAb (Francisco, J. A. et al. Cancer Res. 2000, 60, 3225-3231) or other anti-CD40 antibodies, for example, as those disclosed in U.S. Patent Application Publication Nos. 2003/0211100 and 2002/0142358, mAb to the CD70 antigen, for example, 1F6 mAb and 2F2 mAb, and mAb to the CD30 antigen, for example, AC10 (Bowen, M. A. et al. J. Immunol. 1993, 151, 5896-5906, Wahl, A. F. et al. Cancer Res. 2002, 62(13), 3736-3742) or MDX-0060 (U.S. Patent Application Publication No. 2004/0006215).

m in formula (12) or formula (13) of the invention is 0 or 1. In a preferred embodiment, m is 0, and a conjugate represented by formula (32) or formula (33) is provided.

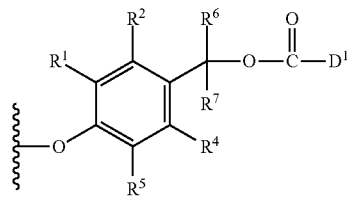
(32)

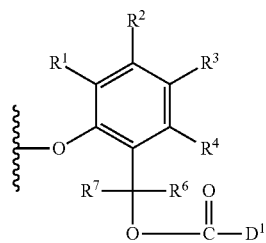
(33)

In another preferred embodiment of the aspect, m is 1 and $B^2$ is a hydrogen atom, and a conjugate represented by formula (34) or formula (35) is provided.

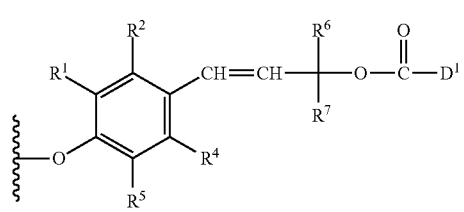
(34)

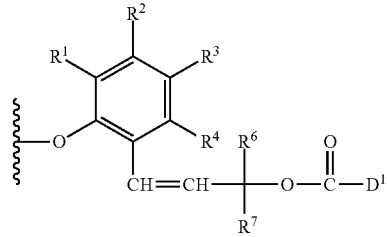
(35)

In still another preferred embodiment of the aspect, m is 1 and $B^2$ is $-C(R^6)(R^7)OC(O)D^1$, and a conjugate represented by formula (36) or formula (37) is provided. In the embodiment, a derivative having two $E^1$ with respect to one acetal is provided.

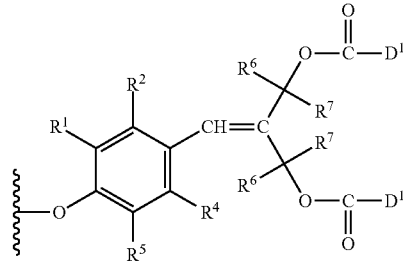
(36)

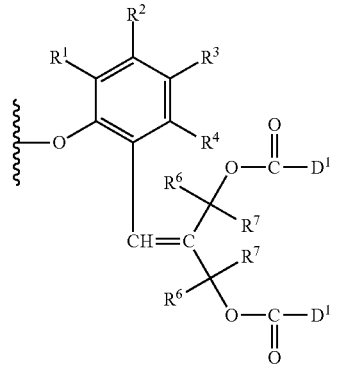
(37)

EXAMPLES

The invention will be described more specifically with reference to the examples, but the invention should not be construed as being limited thereto.

In $^1$H-NMR analysis, JNM-ECP400 or JNM-ECA600 manufactured by JEOL DATUM Ltd. was used. For the measurement, a tube of 5 mm 0 was used, and tetramethylsilane (TMS) was used as an internal standard substance in the case where a deuterated solvent was $CDCl_3$ or $d_6$-DMSO, or HDO was used as a standard in the case of $D_2O$.

In gel permeation chromatography (GPC) analysis, there were used SHODEX GPC SYSTEM-11 as a GPC system, SHODEX RIX8 as a differential refractometer which was a detector, and three columns, i.e., SHODEX KF801L, KF803L and KF804L (φ8 mm×300 mm) connected in series as GPC columns, and the temperature of the column oven was set to 40° C. The measurement was performed using tetrahydrofuran as an eluent, at the flow rate of 1 ml/minute, at the sample concentration of 0.1% by weight, and in the injection volume of 0.1 ml. The calibration curves prepared by using ethylene glycol, diethylene glycol and triethylene glycol manufactured by Kanto Chemical Co., Ltd. and Polymer Standards for GPC of polyethylene glycol or polyethylene oxide having a molecular weight of 600 to 70,000 manufactured by Polymer Laboratory Co., Ltd. were used. For analysis of data, BORWIN GPC calculation program was used. Mn represents a number average molecular weight, Mw represents a weight average molecular weight, and a molecular weight distribution is indicated as a calculated value of Mw/Mn.

A citrate deuterated water buffer having pD of 3.0, an acetate deuterated water buffer having pD of 4.0 and a deuterated water buffer of HEPES (2-[4-(Hydroxyethyl)-1-piperazinyl]ethanesulfonic acid) having pD of 7.4 for use in the hydrolysis test were prepared by adding a 0.1M sodium hydroxide deuterated water solution to a 0.1M citric acid deuterated water solution, a 0.1M acetic acid deuterated water solution and a 0.1M HEPES deuterated water solution, respectively, based on the relational equation shown below described in "Glasoe, P. K.; Long, F. A. J. Phys. Chem. 1960, 64, 188-190".

$pD$=Measured value by pH meter+0.40

A release rate of benzylamine was evaluated by $^1$H-NMR using a compound of formula (44) and calculated according to a formula shown below by taking an integral value of methylene hydrogen of benzylamine in the compound of formula (44) as $I^1$ and an integral value of methylene hydrogen of benzylamine released upon 1,6-benzyl elimination caused by the hydrolysis of acetal as $I^2$.

Release rate of benzylamine (%)=$[I^2/(I^1+I^2)]\times 100$

Example 1

Into a 50 mL three-necked flask equipped with a thermometer, a nitrogen inlet tube, a stirrer and a condenser tube were charged 3-hydroxybezaldehyde (2.00 g, 16.4 mmol), trimethyl orthoformate (3.48 g, 32.8 mmol) and methanol (17 g), p-toluenesulfonic acid monohydrate (0.312 mg, 1.64 mmol) was added thereto, and the reaction was performed at 25° C. for 2 hours. Sodium hydroxide was added thereto and after the mixture was stirred for a while, the solvent was distilled off under a reduced pressure. The reside was dissolved in dichloromethane, the solution was washed in order with an aqueous 5% by weight sodium hydrogen carbonate solution and an aqueous 25% by weight sodium chloride solution, and the organic layer was dried over anhydrous sodium sulfate. After filtration, the solvent was distilled off under a reduced pressure to obtain a compound of formula (38).

$^1$H-NMR (CDCl$_3$, internal standard TMS); δ (ppm):
3.33 (6H, s, —OC$\underline{H}_3$),
5.35 (1H, s, —C$\underline{H}$<)
6.81 (1H, d, arom.$\underline{H}$)
6.95 (1H, d, arom.$\underline{H}$)
7.23-7.26 (1H, m, arom.$\underline{H}$)

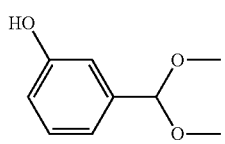

(38)

Example 2

Into a 50 mL three-necked flask equipped with a thermometer, a nitrogen inlet tube, a stirrer and a condenser tube were charged 2,4-di(hydroxymethyl)phenol (50.0 mg, 0.324 mmol) synthesized according to a literature procedure (Freeman, J. H.; J. Am. Chem. Soc. 1952, 74, 6257-6260), the compound of formula (38) (217 mg, 1.29 mmol), 2,6-di-tert-butyl-p-cresol (7.14 mg, 0.0324 mmol), anhydrous sodium sulfate (1 g) and cyclopentyl methyl ether (10 g), p-toluenesulfonic acid monohydrate (4.10 mg, 0.0212 mmol) was added thereto, and the reaction was performed at 40° C. for 2 hours. N-methylmorpholine was added thereto and the mixture was stirred for a while and then filtered. The mixture was washed with an aqueous 10% by weight sodium chloride solution, and the organic layer was dried over anhydrous sodium sulfate. After filtration, the solvent was distilled off under a reduced pressure to obtain a compound of formula (39).

$^1$H-NMR (d$_6$-DMSO, internal standard TMS); δ (ppm):
4. 42 (2H, d, —C$\underline{H}_2$OH),
4. 93 (1H, d, —C$\underline{H}_2$O—),
5. 10 (1H, t, —CH$_2$O$\underline{H}$),
5. 15 (1H, d, —C$\underline{H}_2$O—),
6. 01 (1H, s, —C$\underline{H}$<),
6. 80-7.21 (7H, m, arom.$\underline{H}$),
9. 53 (1H, bs, >C—O$\underline{H}$)

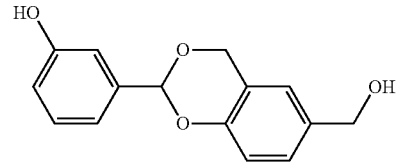

(39)

Example 3

Into a 300 mL four-necked flask equipped with a thermometer, a nitrogen inlet tube, a stirrer and a condenser tube were charged dehydrated methanol (12.8 g, 0.400 mol), dehydrated toluene (150 g) and metal sodium (0.3 g, 13 mmol), and the mixture was stirred at room temperature until the metal sodium was dissolved while bubbling nitrogen through the mixture. The solution was charged into a 5 L autoclave and after the inside of the system was substituted with nitrogen, temperature was raised to 100° C. After adding ethylene oxide (1,987 g, 45 mol) at 100 to 130° C. under a pressure of 1 MPa or less, the reaction was further continued for 2 hours. After the unreacted ethylene oxide gas was removed under a reduced pressure, the mixture was cooled to 60° C., and pH was adjusted to 7.5 with an aqueous 85% phosphoric acid solution to obtain a compound of formula (40).

$^1$H-NMR (CDCl$_3$, internal standard TMS); δ (ppm):
2.68 (1H, t, O$\underline{H}$),
3.38 (3H, s, C$\underline{H}_3$O—),
3.49-3.85 (450$\underline{H}$, m, —(OC$\underline{H}_2$C$\underline{H}_2$)$_n$—)
GPC analysis;
Number average molecular weight (Mn): 5119,
Weight average molecular weight (Mw): 5226,
Polydispersity (Mw/Mn): 1.021

CH$_3$—(OCH$_2$CH$_2$)$_n$—OH     (40)

n=about 113

Example 4

Into a 500 mL three-necked flask equipped with a thermometer, a nitrogen inlet tube, a stirrer, a Dean-stark tube and a condenser tube were charged the compound of formula (40) (100 g, 20.0 mmol) and toluene (250 g), and water was removed by azeotropic distillation with toluene. After cooling to 40° C., triethylamine (3.24 g, 32.0 mmol) was charged and methanesulfonyl chloride (2.75 g, 24.0 mmol) prepared in a dropping funnel was gradually added dropwise thereto. After the completion of the dropwise addition, the reaction was performed at 40° C. for 3 hours. Ethanol (1.11 g, 24.0 mmol) was added thereto and the mixture was stirred for a while, filtered, and diluted with ethyl acetate (200 g). Crystallization was performed by adding hexane (500 g), and after filtration, the crystals were dissolved in ethyl acetate (500 g). Crystallization was again performed by adding hexane (500 g), and after filtration, the crystals were dried under a reduced pressure to obtain a compound of formula (41).

$^1$H-NMR (CDCl$_3$, internal standard TMS); δ (ppm):
3.08 (3H, s, —OSO$_2$C$\underline{H}_3$),
3.38 (3H, s, C$\underline{H}_3$O—),
3.52-3.85 (448H, m, —(OC$\underline{H}_2$C$\underline{H}_2$)$_n$—OC$\underline{H}_2$—),
4.37-4.39 (2H, m, —C$\underline{H}_2$OSO$_2$CH$_3$)
GPC analysis;
Number average molecular weight (Mn): 5197,
Weight average molecular weight (Mw): 5306,
Polydispersity (Mw/Mn): 1.021

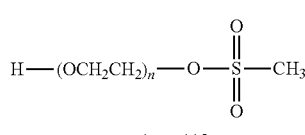

(41)

n = about 113

Example 5

Into a 50 mL three-necked flask equipped with a thermometer, a nitrogen inlet tube, a stirrer and a condenser tube were charged the compound of formula (39) (37.0 mg, 0.141 mmol), the compound of formula (41) (705 mg, 0.141 mmol), potassium carbonate (97.0 mg, 0.705 mmol) and acetonitrile (3.5 g), and the reaction was performed at 80° C. for 4 hours. After filtration, the solvent was distilled off under a reduce pressure, and the residue was dissolved in dichloromethane. The solution was washed with an aqueous 10% by weight sodium chloride solution, and then the organic layer was dried over anhydrous sodium sulfate. After filtration, the solvent was distilled off under a reduced pressure, and the residue was dissolved in toluene (50 g). Crystallization was performed by adding hexane (50 g), and after filtration, the crystals were dried under a reduced pressure to obtain a compound of formula (42).

$^1$H-NMR (CDCl$_3$, internal standard TMS); δ (ppm):
3.38 (3H, s, —OC$\underline{H}_3$),
3.52-4.18 (450H, m, —(OC$\underline{H}_2$C$\underline{H}_2$)$_n$—),
4.62 (2H, s, —C$\underline{H}_2$OH),
4.98 (1H, d, —C$\underline{H}_2$O—),
5.18 (1H, d, —C$\underline{H}_2$O—),
5.95 (1H, s, —C$\underline{H}$<),
6.87-7.34 (7H, m, arom.$\underline{H}$)
GPC analysis;
Number average molecular weight (Mn): 5375,
Weight average molecular weight (Mw): 5490,
Polydispersity (Mw/Mn): 1.021

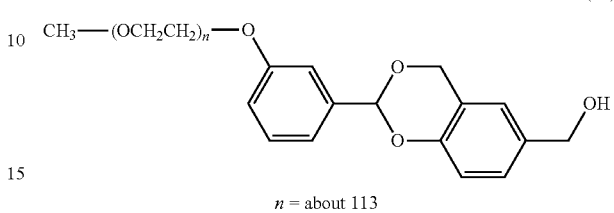

(42)

n = about 113

Example 6

Into a 50 mL three-necked flask equipped with a thermometer, a nitrogen inlet tube, a stirrer and a condenser tube were charged the compound of formula (42) (300 mg, 0.0600 mmol), di(N-succinimidyl) carbonate (46.0 mg, 0.180 mmol), triethylamine (21.0 mg, 0.208 mmol) and dichloromethane (5 g) and the reaction was performed at 25° C. for 12 hours. After filtration, the solution was washed with an aqueous 5% by weight sodium chloride solution, and the solvent of the organic layer was distilled off under a reduced pressure. The residue was dissolved in ethyl acetate (6 g), and the solution was dried over anhydrous sodium sulfate, followed by filtration. After adding ethyl acetate (44 g), crystallization was performed by adding hexane (50 g), and after filtration, the crystals were dried under a reduced pressure to obtain a compound of formula (43).

$^1$H-NMR (CDCl$_3$, internal standard TMS); δ (ppm):
2.58 (4H, s, —COC$\underline{H}_2$C$\underline{H}_2$CO—),
3.38 (3H, s, —OC$\underline{H}_3$),
3.52-4.18 (450H, m, —(OC$\underline{H}_2$C$\underline{H}_2$)$_n$—),
5.00 (1H, d, —C$\underline{H}_2$OCH<),
5.18 (1H, d, —C$\underline{H}_2$O—),
5.25 (2H, s, —C$\underline{H}_2$OCO—),
5.97 (1H, s, —C$\underline{H}$<),
6.96-7.35 (7H, m, arom.$\underline{H}$)
GPC analysis;
Number average molecular weight (Mn): 5516,
Weight average molecular weight (Mw): 5634,
Polydispersity (Mw/Mn): 1.021

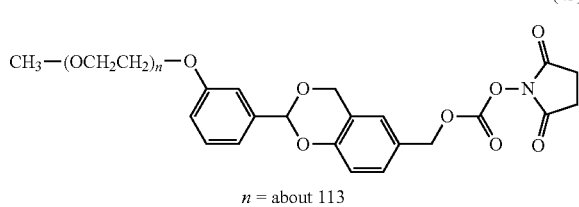

(43)

n = about 113

Example 7

Into a 50 mL three-necked flask equipped with a thermometer, a nitrogen inlet tube, a stirrer and a condenser tube were charged the compound of formula (43) (72.0 mg, 0.0144 mmol), benzylamine (6.17 mg, 0.0576 mmol) and toluene (5 g), and the reaction was performed at 40° C. for 1 hour. After filtration, ethyl acetate (50 g) was added thereto, and crystallization was performed by adding hexane (50 g). After filtration, the crystals were dried under a reduced pressure to obtain a compound of formula (44).

$^1$H-NMR (CDCl$_3$, internal standard TMS); δ (ppm):
3.38 (3H, s, —OC$\underline{H}_3$),
3.52-4.18 (450H, m, —(OCH$_2$CH$_2$)$_n$—),
4.82 (2H, s, —NH—C$\underline{H}_2$—),
4.98 (1H, d, —C$\underline{H}_2$OCH<),
5.07 (2H, s, —C$\underline{H}_2$OCO—),
5.17 (1H, d, —C$\underline{H}_2$O—),
5.95 (1H, s, —C$\underline{H}$<),
6.93-7.35 (12H, m, arom.$\underline{H}$)
GPC analysis;
Number average molecular weight (Mn): 5508,
Weight average molecular weight (Mw): 5625,
Polydispersity (Mw/Mn): 1.021

(44)

CH$_3$—(OCH$_2$CH$_2$)$_n$—O n = about 113

Example 8

Compound (20 mg) of formula (44) was dissolved in a citrate deuterated water buffer (1 mL) having pD of 3.0, an acetate deuterated water buffer (1 mL) having pD of 4.0 and a deuterated water buffer of HEPES (1 mL) having pD of 7.4, respectively. The solutions were allowed to stand in a thermostatic bath at 37° C., and a release rate of benzylamine caused by the hydrolysis of acetal was measured by $^1$H-NMR. The results of measurement were shown in FIG. 6.

Figure 6:
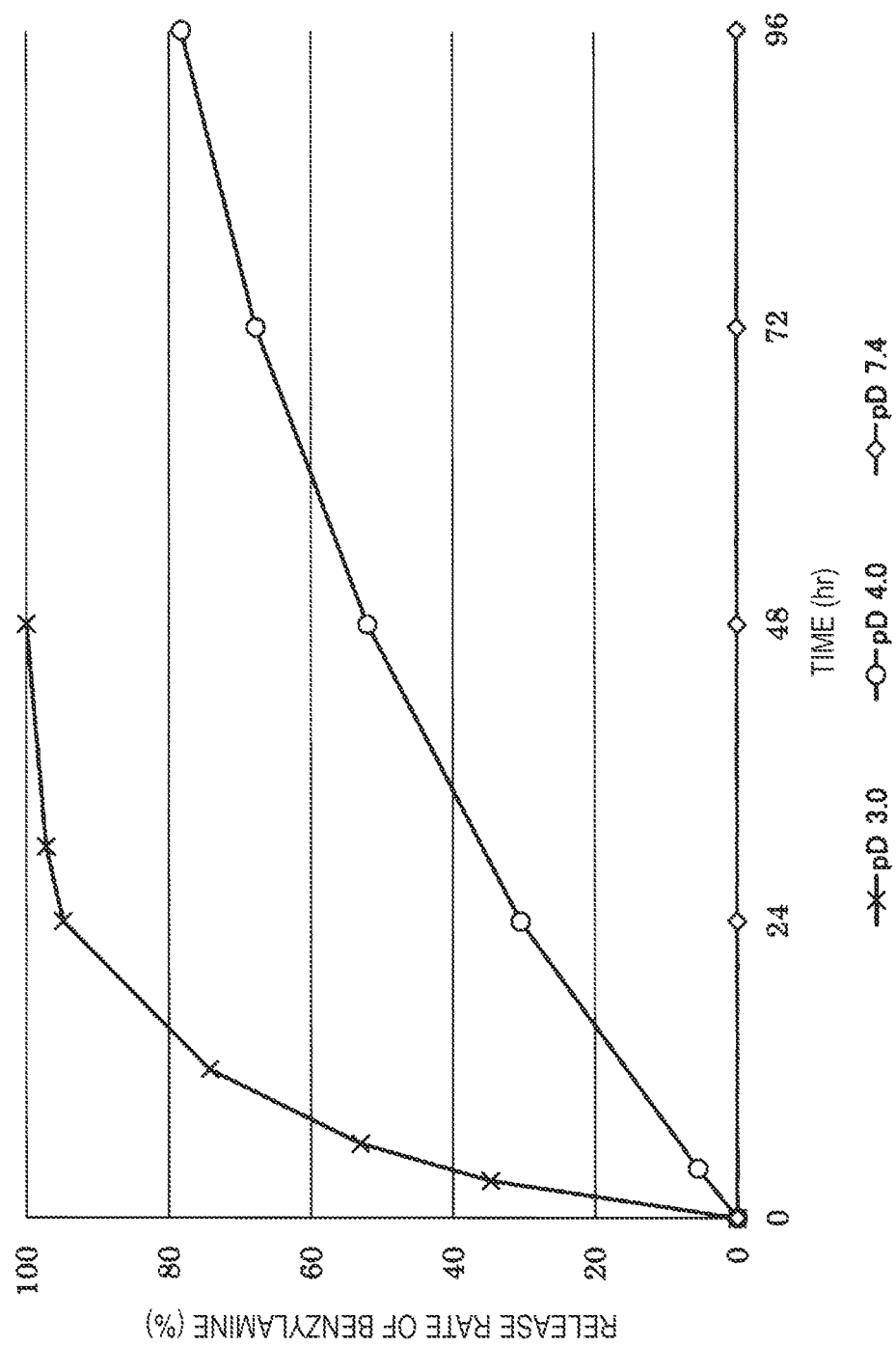
FIG. 6 shows results of release test of benzylamine at 37° C. in a heavy water buffer solution of pD 3.0, 4.0 or 7.4 using a compound of formula (44) described in the example.

As shown in FIG. 6, the compound of formula (44) released benzylamine upon 1,6-benzyl elimination caused by the hydrolysis of acetal at pD 3.0 and pD 4.0, and half-lives (t$_{1/2}$) of benzylamine release were 6 hours and 44 hours, respectively. Hydrolysis was not observed even after 96 hours at pD 7.4.

While the invention has been described in detail and with reference to specific embodiments thereof, it will be apparent to those skilled in the art that various changes and modifications can be made therein without departing from the spirit and scope of the invention.

This application is based on a Japanese patent application filed on Mar. 30, 2017 (Japanese Patent Application No. 2017-067636, and the whole contents thereof are incorporated herein by reference. Also, all the references cited herein are incorporated as a whole.

The invention claimed is:

1. A hydrophilic polymer derivative comprising a hydrophilic polymer moiety and an acetal moiety, wherein the hydrophilic polymer derivative comprises a structure represented by formula (1) or formula (2):

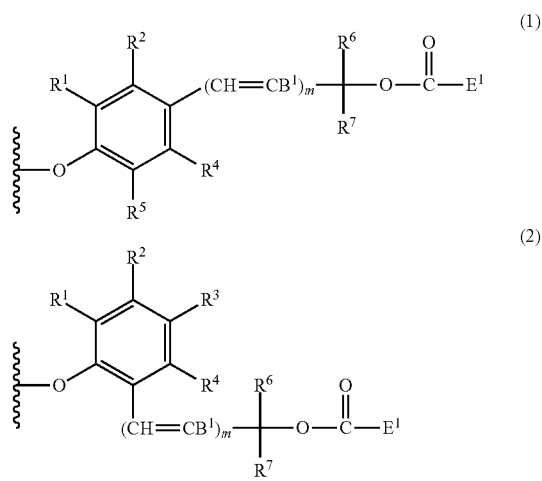

wherein, in the formula (1) and the formula (2), B$^1$ is a hydrogen atom or —C(R$^6$)(R$^7$)OC(O)E$^1$; E$^1$ is a leaving group; R$^1$ is a hydrocarbon group having from 1 to 10 carbon atoms or a hydrogen atom, or R$^1$ may be bonded to an oxygen atom of the acetal moiety; R$^2$, R$^3$, R$^4$, R$^5$, R$^6$ and R$^7$ are each independently a hydrocarbon group having from 1 to 10 carbon atoms or a hydrogen atom; m is 0 or 1; one of two oxygen atoms contained in the acetal moiety is bonded to the phenyl group; and a wavy line represents a covalent bond to a carbon atom bonded to both of the oxygen atoms contained in the acetal moiety.

2. The hydrophilic polymer derivative as claimed in claim 1, which is represented by formula (3) or formula (4):

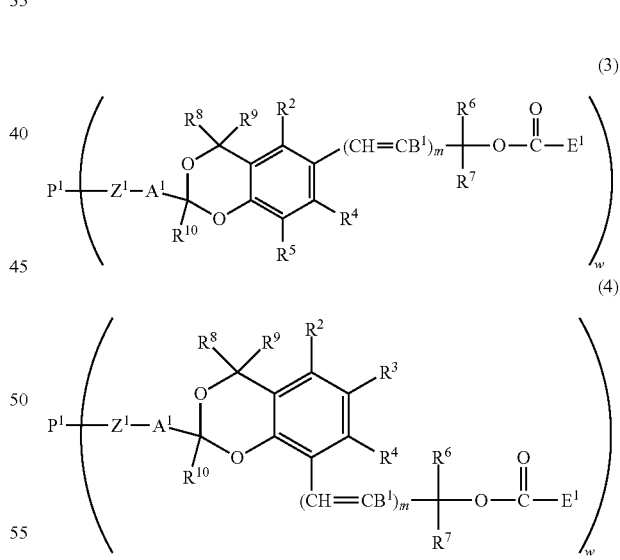

wherein, in the formula (3) and the formula (4), P$^1$ is the hydrophilic polymer moiety; w is an integer of 1 to 20; Z$^1$ is an ether bond, an ester bond, a carbonate bond, a urethane bond, an amide bond, a secondary amino group, an alkylene group containing any of these bonds and group, a single bond or an alkylene group; A$^1$ is a divalent hydrocarbon group having from 1 to 10 carbon atoms or a phenylene group which may have a substituent; R$^8$ and R$^9$ are each independently a hydrocarbon group having from 1 to 9 carbon atoms or a hydrogen atom; and $R^{10}$ is a hydrocarbon group having from 1 to 10 carbon atoms or a hydrogen atom.

3. The hydrophilic polymer derivative as claimed in claim 1, which is represented by formula (5) or formula (6):

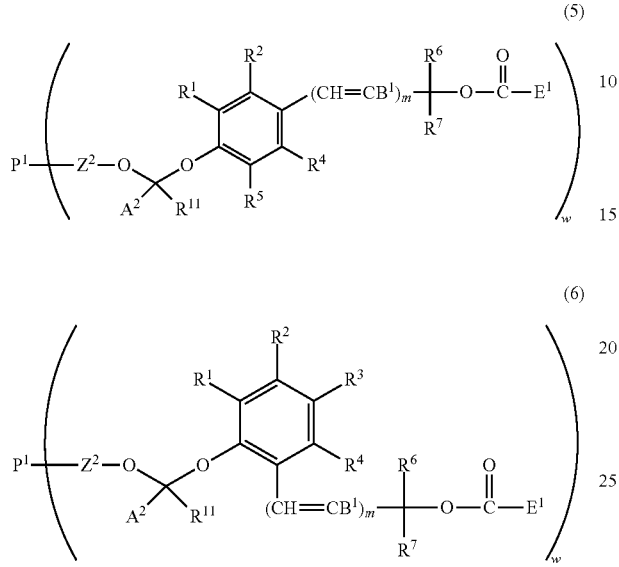

wherein, in the formula (5) and formula (6), $P^1$ is the hydrophilic polymer moiety; w is an integer of 1 to 20; $Z^2$ is an ether bond, an ester bond, a carbonate bond, a urethane bond, an amide bond, a secondary amino group, an alkylene group containing any of these bonds and group, a single bond or an alkylene group; $A^2$ is a hydrocarbon group having from 1 to 10 carbon atoms or a phenylene group which may have a substituent; and $R^{11}$ is a hydrocarbon group having from 1 to 10 carbon atoms or a hydrogen atom.

4. The hydrophilic polymer derivative as claimed in claim 2, wherein $P^1$ is a straight-chain polyethylene glycol having a hydrocarbon group or a chemically reactive functional group at a terminal.

5. The hydrophilic polymer derivative as claimed in claim 4, wherein w is 1 and $P^1$ is represented by formula (7) or formula (8):

wherein, in the formula (7), $Y^1$ is a hydrocarbon group having from 1 to 24 carbon atoms, and n is an integer of 3 to 2,000;

wherein, in the formula (8), $X^1$ is a chemically reactive functional group, $Z^3$ is a divalent spacer, and n is an integer of 3 to 2,000.

6. The hydrophilic polymer derivative as claimed in claim 2, wherein $P^1$ is a branched polyethylene glycol having a hydrocarbon group or a chemically reactive functional group at a terminal.

7. The hydrophilic polymer derivative as claimed in claim 6, wherein w is 1 and $P^1$ is represented by formula (9) or formula (10):

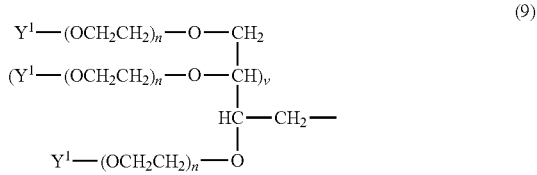

wherein, in the formula (9), $Y^1$ is a hydrocarbon group having from 1 to 24 carbon atoms, n is an integer of 3 to 1,000, and v is 0 or 2;

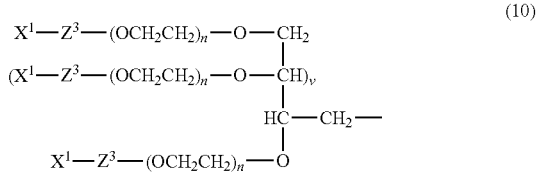

wherein, in the formula (10), $X^1$ is a chemically reactive functional group, $Z^3$ is a divalent spacer, n is an integer of 3 to 1,000, and v is 0 or 2.

8. The hydrophilic polymer derivative as claimed in claim 6, wherein w is v+2 and $P^1$ is represented by formula (11):

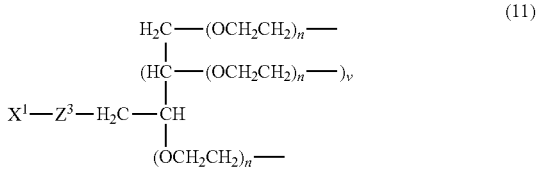

wherein, in the formula (11), $X^1$ is a chemically reactive functional group, $Z^3$ is a divalent spacer, n is an integer of 3 to 1,000, and v is 0 or 2.

9. The hydrophilic polymer derivative as claimed in claim 5, wherein $X^1$ is selected from the group consisting of a maleimide group, an α-haloacetyl group, an acryl group, a vinyl sulfone group, a protected thiol group, a pyridyldithio group, an aldehyde group, a carboxy group, a protected carboxy group, a protected amino group, a protected oxyamino group, a protected hydrazide group, an azide group, an allyl group, a vinyl group, an alkynyl group and a hydroxy group.

10. The hydrophilic polymer derivative as claimed in claim 5, wherein $X^1$ is selected from the group consisting of formula (a), formula (b), formula (c), formula (d), formula (e), formula (f), formula (g), formula (h), formula (i), formula (j), formula (k), formula (l), formula (m), formula (n) and formula (o):

(b) 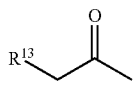

(c) 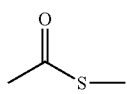

(d) 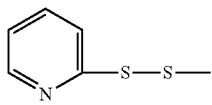

(e) 

(f) 

(g) 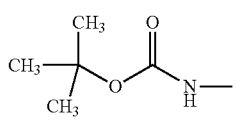

(h) 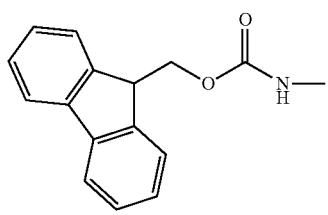

(i) 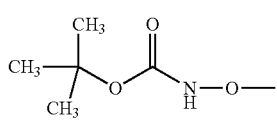

(j) 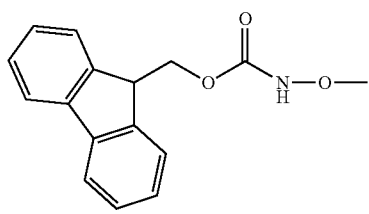

(k) 

(l) 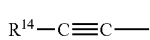

(m) 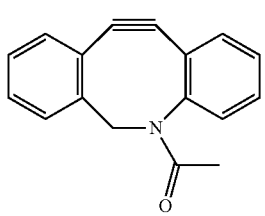

(n) 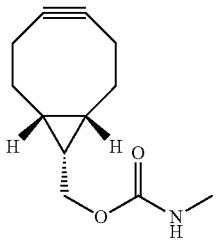

(o) 

wherein, in the formula (a), $R^{12}$ is a hydrogen atom or a hydrocarbon group having from 1 to 5 carbon atoms; in the formula (b), $R^{13}$ is a halogen atom selected from a chlorine atom, a bromine atom and an iodine atom; and in the formula (l), $R^{14}$ is a hydrogen atom or a hydrocarbon group having from 1 to 5 carbon atoms.

11. The hydrophilic polymer derivative as claimed in claim 5, wherein $Z^3$ is an ether bond, an ester bond, a carbonate bond, a urethane bond, an amide bond, a secondary amino group, an alkylene group containing any of these bonds and group, a single bond or an alkylene group.

12. The hydrophilic polymer derivative as claimed in claim 2, wherein $P^1$ is a polyethylene glycol having a number of terminals of 2 to 8, all the terminals of the polyethylene glycol constituting $P^1$ are each connected to $Z^1$, and w is equal to the number of terminals of the polyethylene glycol.

13. The hydrophilic polymer derivative as claimed in claim 12, wherein $P^1$ is selected from the group consisting of formula (r), formula (s), formula (t), formula (u) and formula (v):

(r) $\quad$ —$(OCH_2CH_2)_n$—

(s)
$H_2C$—$(OCH_2CH_2)_n$—
$HC$—$(OCH_2CH_2)_n$—
$H_2C$—$(OCH_2CH_2)_n$—

(t)
$\qquad (OCH_2CH_2)_n$—
$H_2C\diagup$
$\qquad \diagdown CH_2$—$(OCH_2CH_2)_n$—
$\qquad\qquad C$
$H_2C\diagup \diagup CH_2$—$(OCH_2CH_2)_n$—
$\qquad \diagdown (OCH_2CH_2)_n$—

(u)
$H_2C$—$(OCH_2CH_2)_n$—
$HC$—$(OCH_2CH_2)_n$—
$H_2C$
$|$
$O$
$|$
$H_2C$
$HC$—$(OCH_2CH_2)_n$—
$H_2C$—$(OCH_2CH_2)_n$—

-continued

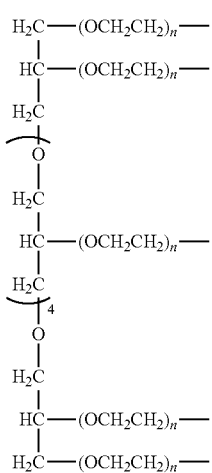

(v)

wherein, in the formulae, n is an integer of 3 to 2,000, w is 2 in a case where $P^1$ is represented by the formula (r), w is 3 in a case where $P^1$ is represented by the formula (s), w is 4 in a case where $P^1$ is represented by the formula (t), w is 4 in a case where $P^1$ is represented by the formula (u), and w is 8 in a case where $P^1$ is represented by the formula (v).

14. A conjugate comprising a structure represented by formula (12) or formula (13) which is obtained by reacting —OC(O)$E^1$ group of a hydrophilic polymer derivative comprising a structure represented by formula (1) or formula (2) with an amino group contained in a biofunctional molecule:

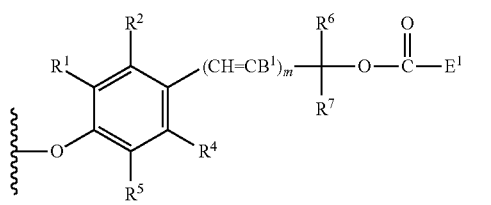

(1)

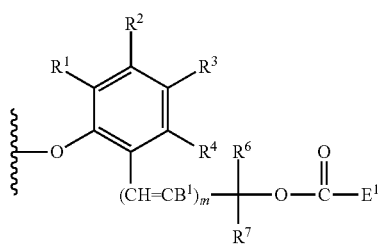

(2)

wherein, in the formula (1) and the formula (2), $B^1$ is a hydrogen atom or —C($R^6$)($R^7$)OC(O)$E^1$; $E^1$ is a leaving group; $R^1$ is a hydrocarbon group having from 1 to 10 carbon atoms or a hydrogen atom, or $R^1$ may be bonded to an oxygen atom of the acetal moiety; $R^2$, $R^3$, $R^4$, $R^5$, $R^6$ and $R^7$ are each independently a hydrocarbon group having from 1 to 10 carbon atoms or a hydrogen atom; m is 0 or 1; one of two oxygen atoms contained in the acetal moiety is bonded to the phenyl group; and a wavy line represents a covalent bond to a carbon atom bonded to both of the oxygen atoms contained in the acetal moiety,

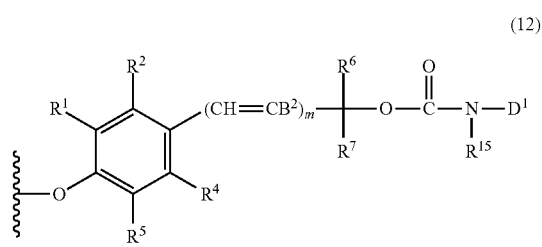

(12)

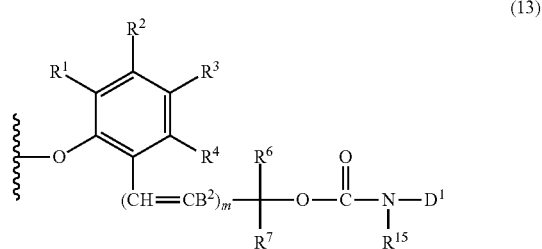

(13)

wherein, in the formula (12) and the formula (13), $B^2$ is a hydrogen atom or —C($R^6$)($R^7$)OC(O)$D^1$; $R^1$ is a hydrocarbon group having from 1 to 10 carbon atoms or a hydrogen atom, or $R^1$ may be bonded to an oxygen atom of the acetal moiety; $R^2$, $R^3$, $R^4$, $R^5$, $R^6$, $R^7$ and $R^{15}$ are each independently a hydrocarbon group having from 1 to 10 carbon atoms or a hydrogen atom; m is 0 or 1; a wavy line represents a covalent bond to a carbon atom bonded to both of the oxygen atoms contained in the acetal moiety; and $D^1$ is a residue obtained by eliminating an amino group constituting a carbamate bond among amino groups contained in the biofunctional molecule.

* * * * *